US008330026B2

(12) United States Patent
Wallach et al.

(10) Patent No.: US 8,330,026 B2
(45) Date of Patent: Dec. 11, 2012

(54) DERIVATIVES OF THE NF-κB INDUCING ENZYME, THEIR PREPARATION AND USE

(75) Inventors: David Wallach, Rehovot (IL); Parameswaran Ramakrishnan, Rehovot (IL); Taisia Shmushkovich, Rehovot (IL)

(73) Assignee: Yeda Research and Development Co., Ltd., Weizmann Institute of Science, Rehovot (IL)

( * ) Notice: Subject to any disclaimer, the term of this patent is extended or adjusted under 35 U.S.C. 154(b) by 0 days.

(21) Appl. No.: 10/511,314

(22) PCT Filed: Apr. 15, 2003

(86) PCT No.: PCT/IL03/00317
§ 371 (c)(1),
(2), (4) Date: May 17, 2005

(87) PCT Pub. No.: WO03/087380
PCT Pub. Date: Oct. 23, 2003

(65) Prior Publication Data
US 2005/0272633 A1    Dec. 8, 2005

(30) Foreign Application Priority Data

Apr. 18, 2002  (IL) .......................... 149217
Oct. 8, 2002  (IL) .......................... 152183

(51) Int. Cl.
*C07K 1/00*  (2006.01)
(52) U.S. Cl. ........................................ 930/10
(58) Field of Classification Search .................. None
See application file for complete search history.

(56) References Cited

U.S. PATENT DOCUMENTS

| 5,843,721 | A | 12/1998 | Rothe et al. |
| 5,844,073 | A | 12/1998 | Rothe et al. |
| 5,854,003 | A | 12/1998 | Rothe et al. |
| 7,485,456 | B1 | 2/2009 | Wallach et al. |

FOREIGN PATENT DOCUMENTS

| EP | 0 578 932 A2 | 1/1994 |
| JP | 2000507826 | 6/2000 |
| JP | 2001510348 | 7/2001 |
| WO | 9737016 A1 | 10/1997 |

OTHER PUBLICATIONS

O'Neill et al Signal transduction pathways activated by the IL-1 receptor family: ancient signaling machinery in mammals, insects, and plants. J Leukoc Biol. Jun. 1998;63(6):650-7. Review.*
O'Shea et al, Cytokines and Autoimmunity Nature Reviews Immunology 2, 37-45 (2002).*
Yamada et al, Abnormal immune function of hemopoietic cells from alymphoplasia (aly) mice, a natural strain with mutant NF-kappa B-inducing kinase. J Immunol. Jul. 15, 2000;165(2):804-12.*
Tinubu et al, Humanized antibody directed to the IL-2 receptor beta-chain prolongs primate cardiac allograft survival. J Immunol. Nov. 1, 1994;153(9):4330-8.*
Waldmann et al, The interleukin-2 receptor: a target for monoclonal antibody treatment of human T-cell lymphotrophic virus I-induced adult T-cell leukemia. Blood. Sep. 15, 1993;82(6):1701-12.*
Luftig et al, Effects of the NIK aly mutation on NF-kappaB activation by the Epstein-Barr virus latent infection membrane protein, lymphotoxin beta receptor, and CD40. J Biol Chem. May 4, 2001;276(18):14602-6. Epub Mar. 14, 2001.*
Rothe et al.,"A Novel Family of Putative Signal Transducers Associated with the Cytoplasmic Domain of the 75 kDa Tumor Necrosis Factor Receptor" Cell, 78: 681-692 (1994).
Smith.,"Filamentous Fusion Phage: Novel Expression Vectors That Display Cloned Antigens on the Virion Surface" Science, 228:1315-17 (1984).
Fields et al.,"A novel genetic system to detect protein-protein interactions" Nature, 340: 265-6 (1989).
Akiba et al., "CD27, a Member of the Tumor Necrosis Factor Receptor Superfamily, Activates NF-kB and Stress-activated Protein Kinase/c-Jun N-terminal Kinase via TRAF2, TRAF5, and NF-kB-inducing Kinase" J. Biol Chem, 273 (21): 13353-13358 (1998).
Baldwin, Jr., "The NF-kB and IkB Proteins: New Discoveries and Insights" Annu. Rev. Immunol, 14: 649-83 (1996).
Ghosh et al., "NF-kB and REL Proteins: Evolutionarily Conserved Mediators of Immune Responses" Annu. Rev. Immunol, 16:225-60 (1998).
Karin et al., "Phosphorylation Meets Ubiquitination: The Control of NF-kB Activity" Ann. Rev. Immunol, 18:621-663 (2000).
Canicio et al.,"Nuclear Factor kB-inducing Kinase and IkB Kinase-a Signal Skeletal Muscle Cell Differentiation" J Biol Chem, 276(23): 20228-33 (2001).
Darnay et al.,"Activation of NF-kB by RANK Requires Tumor Necrosis Factor Receptor-associated Factor (TRAF) 6 and NF-kB-inducing Kinase" J Biol Chem, 274, 12:7724-31 (1999).
DiSanto et al., "Lymphoid development in mice with a targeted deletion of the interleukin 2 receptor gamma chain", Proc. Natl. Acad. Sci., 92:377-381 (1995).
Fagarasan et al., "Alymphoplasia (aly)-type Nuclear Factor kB-inducing (NIK) Kinase Causes Defects in Secondary Lymphoid Tissue Chemokine Receptor Signaling and Homing of Peritoneal Cells to the Gut-associated Lymphatic Tissue System", J. Exp. Med., vol. 191, 1477-86 (2000).
Foehr et al., "The NF-kB-inducing Kinase Induces PC12 Cell Differentiation and Prevents Apoptosis", J Biol Chem, vol. 275 (44): 34021-24 (2000).
Matsushima et al., "Essential Role of Nuclear Factor (NF)-k B-inducing Kinase and Inhibitor of kB (IkB) Kinase a in NFk B Activation through Lymphotoxin b Receptor, but Not through Tumor Necrosis Factor Receptor I", J. Exp. Med. vol. 193, 5:631-636 (2001).
Mercurio et al., "Multiple signals converging on NF-ICB", Current Opinion in Cell Biology, 11:226-232 (1999).
Natoli et al., "Tumor Necrosis Factor (TNF) Receptor 1 Signaling Downstream of TNF Receptor-associated Factor 2: Nuclear Factor kB (NFkB)-Inducing Kinase Requirement for Activation of Activating Protein 1 and NFkB But Not of c-Jun N-Terminal Kinase/Stress-Activated Protein Kinase" J Biol Chem, vol. 272(42):26079-26082 (1997).

(Continued)

*Primary Examiner* — Sheridan Swope
(74) *Attorney, Agent, or Firm* — Browdy and Neimark, P.L.L.C.

(57) ABSTRACT

The invention relates to the use of NF-κB inducing kinase (NIK) and related molecules for the modulation of signal activities controlled by cytokines, and some new such molecules.

8 Claims, 11 Drawing Sheets

OTHER PUBLICATIONS

Pahl et al., "Activators and target genes of Rel/NF-kB transcription factors" Oncogene, vol. 18: 6853-6866 (1999).

Regnier et al.,"Identification and Characterization of an IkB Kinase" Cell, vol. 90:373-383 (1997).

Noguchi et al.,"Interleukin-2 Receptor y Chain Mutation Results in X-Linked Severe Combined Immunodeficiency in Humans" Cell, vol. 73: 147-157 (1993).

Senftleben et al., "Activation by IKKa of a Second, Evolutionary Conserved, NF-kB Signaling Pathway" Science, vol. 293:1495-9 (2001).

Shinkura et al.,"Alymphoplasia is caused by a point mutation in the mouse gene encoding Nf-κb-inducing kinase" Nat Genet, vol. 22:74-7 (1999).

Sylla et al., "Epstein-Barr virus-transforming protein latent infection membrane protein 1 activates transcription factor NF-kB through a pathway that includes the NF-kB-inducing kinase and the IkB kinases IKKa and IKKb" Proc. Natl. Acad. Sci, vol. 95:10106-10111 (1998).

Takeuchi et al.,"Anatomy of TRAF2: Distinct Domains for Nuclear Factor-kB Activation and Association With Tumor Necrosis Factor Signaling Proteins" J Biol Chem,vol. 271(33): 19935-42 (1996).

Uhlik et al.,"NF-kB-inducing Kinase and IkB Kinase Participate in Human T-cell Leukemia Virus I Tax-mediated NF-kB Activation" J Biol Chem, vol. 273(33): 21132-21136 (1998).

Xiao et al.,"Negative Regulation of the Nuclear Factor kB-inducing Kinase by a cis-Acting Domain" J Biol Chem, vol. 275(28): 21081-21085 (2000).

Xiao et al.,"NF-kB-Inducing Kinase Regulates the Processing of NF-kB2 p100" Molecular Cell, vol. 7:401-409 (2001).

Yamada et al.,"Abnormal Immune Function of Hemopoietic Cells from Alymphoplasia (aly) Mice, a Natural Strain with Mutant NF-kB-Inducing Kina" J. Immunol, 165: 804-812 (2000).

Yamamoto et al., "Therapeutic potential of inhibition of the NF-kB pathway in the treatment of inflammation and cancer" The Journal of Clinical Investigation, vol. 107(2): 135-142 (2001).

Yin et al., "Defective Lymphotoxin-b ReceptorÐ Induced NF-kB Transcriptional Activity in NIK-DeÞcient Mice" Science, vol. 291:2162-2165 (2001).

Leonard et al.,"Role of the Common Cytokine Receptor (gamma)Chain in Cytokine Signaling and Lymphoid Development" Immunol Rev, No. 148: 97-114, 1995.

Adang et al.,"The Contribution of Combinatorial Chemistry to Lead Generation: An Interim Analysis" Curr Med Chem, 8:985-998 (2001).

Miyawaki et al.,"A new mutation, aly, that induces a generalized lack of lymph nodes accompanied by immunodeficiency in mice" Eur. J. Immunol, vol. 24: 429-434 (1994).

Garceau et al., "Lineage-restricted.function of nuclear factor kappaB-inducing kinase (NIK) in transducing signals via CD40" J. Exp Med, vol. 191:381-6. (2000).

Geleziunas et al.,"Human T-cell leukemia virus type 1 Tax induction of NF-kappaB involves activation of the IkappaB kinase alpha (IKKalpha) and IKKbeta cellular kinases" Mol Cell Biol, vol. 18: 5157-65. (1998).

Lin et al., "The protooncogene Cot kinase participates in CD3/CD28 induction of NF-kappaB acting through the NF-kappaB-inducing kinase and IkappaB kinases" Immunity, vol. 10:271-80 (1999).

Ling et al., "NF-kappaB-inducing kinase activates IKK-alpha 15 by phosphorylation of Ser-176" Proc Natl Acad Sci, vol. 95:3792-7. (1998).

Malinin et al., "MAP3K-related kinase involved in NF-kappaB induction by TNF, CD95 and IL-I" Nature, 385:540-4. (1997).

Matsumoto et al., "Involvement of distinct cellular 20 compartments in the abnormal lymphoid organogenesis in lymphotoxin-alphadeficient mice and alymphoplasia (aly) mice defined by the chimeric analysis" J. Immunol, 163, 1584-91 (1999).

Rothe et al., "Human NIK protein" Database Geneseq 'Online! EBI, Hinxton, Cambridgeshire, U.K. Database accession No. AAW82497 (Mar. 4, 1999).

Boldin et al., "Amino acid sequence of NF-kappaB inducing kinase" Database Geneseq 'Online!, EBI. Hinxton. Cambridgeshire, U.K.; Database accession No. AAW42402 (Apr. 15, 1998).

Oshea, et al., "Cytokines and autoimmunity", Nature Reviews, vol. 21, pp. 37-45, 2002.

Tinubu, et al., "Humanized antibody directed to trhe IL-2 receptor beta-chain prolongs primate cardiac allograft survival", J. Immunol., vol. 153 (9), pp. 4330-4338, 1994.

Luflig, et al., "Effects of the NIK aly mutation on NK-kapa B activation by the Epstein-Barr virus Latent infection membrane protein lymphotoxin beta receptor, and CD40", J. Biol. Chem, vol. 276(18), pp. 14602-14606, 2001.

Oshea, at al., "Cytokines and autoimmunity", Nature Reviews, vol. 21, pp. 37-45, 2002.

Schreck, et al., "NfκB as Inducible Transcriptional Activator of the Granulocyte-Macrophage Colony-Stimulating Factor Gene", Molecular and Cellular Biology, vol. 10, No. 3, pp. 1281-1286, Mar. 1990.

Tinubu, et al., "Humanized antibody directed to the IL-2 receptor beta-chain prolongs primate cardiac allograft survival", J. Immunol., vol. 153(9), pp. 4330-4338, 1994.

Waldmann, et al., "The interleukin-2 receptor: a target for monoclonal antibody treatment of human T-cell Lymphotrophic virus I induced adult T cell leukemia", Blood, vol. 82(6), pp. 1701-1712, 1993.

* cited by examiner

Figure 11

ERTMPRIPTLKNLEDLVTEYHGNFSAWSGVSKGLAESLQPDYSERLCLVSEIPPK
GGALGEGPGASPCNQHSPYWAPPCYTLKPET

Figure 12

LCLVSEIPPKGGALGEGPGASPCNQHSPYWAPPCYTLKPET

Figure 13

GAACGGACGATGCCCCGAATTCCCACCCTGAAGAACCTAGAGGATCTTGTTA
CTGAATACCACGGGAACTTTTCGGCCTGGAGTGGTGTGTCTAAGGGACTGGC
TGAGAGTCTGCAGCCAGACTACAGTGAACGACTCTGCCTCGTCAGTGAGATT
CCCCCAAAAGGAGGGGCCCTTGGGGAGGGGCCTGGGGCCTCCCCATGCAACC
AGCATAGCCCCTACTGGGCCCCCCATGTTACACCCTAAAGCCTGAAACCTG
A

Figure 14

CTCTGCCTCGTCAGTGAGATTCCCCCAAAAGGAGGGGCCCTTGGGGAGGGGC
CTGGGGCCTCCCCATGCAACCAGCATAGCCCCTACTGGGCCCCCCATGTTAC
ACCCTAAAGCCTGAAACCTGA

Figure 15

WAPPCYTLKPET

CYTOKINE-INDUCED IKK- RECRUITMENT TO THE CγC AND ACTIVATION
PBMC, IL2 TREATMENT
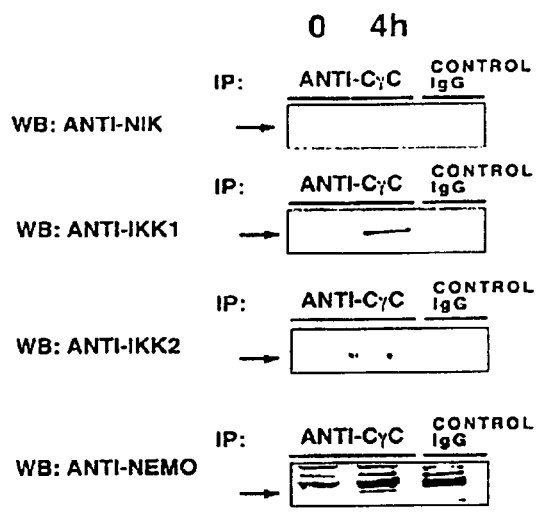
Fig. 16 A
MYC-NIK BJAB, IL15 TREATMENT
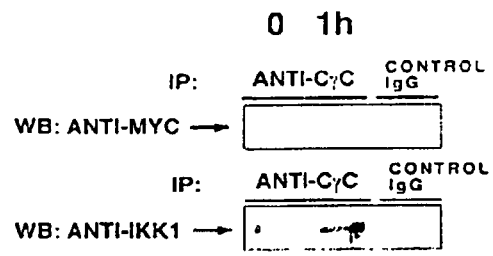
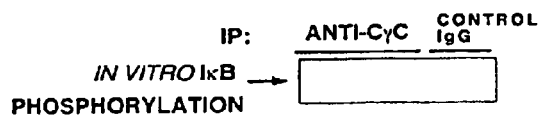
Fig. 16 B

SEQUENCE LISTING

```
<160> NUMBER OF SEQ ID NOS: 19

<210> SEQ ID NO 1
<211> LENGTH: 86
<212> TYPE: PRT
<213> ORGANISM: Homo sapiens

<400> SEQUENCE: 1

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
    50                  55                  60

Ala Ser Pro Cys Asn Gln His Ser Pro Tyr Trp Ala Pro Pro Cys Tyr
65                  70                  75                  80

Thr Leu Lys Pro Glu Thr
                85

<210> SEQ ID NO 2
<211> LENGTH: 41
<212> TYPE: PRT
<213> ORGANISM: Homo sapiens

<400> SEQUENCE: 2

Leu Cys Leu Val Ser Glu Ile Pro Pro Lys Gly Gly Ala Leu Gly Glu
1               5                   10                  15

Gly Pro Gly Ala Ser Pro Cys Asn Gln His Ser Pro Tyr Trp Ala Pro
            20                  25                  30

Pro Cys Tyr Thr Leu Lys Pro Glu Thr
        35                  40

<210> SEQ ID NO 3
<211> LENGTH: 12
<212> TYPE: PRT
<213> ORGANISM: Homo sapiens
```

-continued

```
<400> SEQUENCE: 3

Trp Ala Pro Pro Cys Tyr Thr Leu Lys Pro Glu Thr
1               5                   10

<210> SEQ ID NO 4
<211> LENGTH: 39
<212> TYPE: DNA
<213> ORGANISM: Homo sapiens

<400> SEQUENCE: 4
tgggcccccc catgttacac cctaaagcct gaaacctga                              39

<210> SEQ ID NO 5
<211> LENGTH: 261
<212> TYPE: DNA
<213> ORGANISM: Homo sapiens

<400> SEQUENCE: 5
gaacggacga tgccccgaat cccaccctg aagaacctag aggatcttgt tactgaatac        60
cacgggaact tttcggcctg gagtggtgtg tctaagggac tggctgagag tctgcagcca      120
gactacagtg aacgactctg cctcgtcagt gagattcccc aaaaggagg ggcccttggg       180 gaggggcctg ggcctcccc atgcaaccag catagcccct actgggcccc ccatgttac        240 accctaaagc ctgaaacctg a                                                261

<210> SEQ ID NO 6
<211> LENGTH: 126
<212> TYPE: DNA
<213> ORGANISM: Homo sapiens

<400> SEQUENCE: 6
ctctgcctcg tcagtgagat tcccccaaaa ggaggggccc ttggggaggg gcctggggcc       60
tccccatgca accagcatag cccctactgg gccccccat gttacaccct aaagcctgaa       120
acctga                                                                 126

<210> SEQ ID NO 7
<211> LENGTH: 37
<212> TYPE: DNA
<213> ORGANISM: Homo sapiens

<400> SEQUENCE: 7
ctcgtcagtg agattgccgc aaaaggaggg gcccttg                                37

<210> SEQ ID NO 8
<211> LENGTH: 37
<212> TYPE: DNA
<213> ORGANISM: Homo sapiens

<400> SEQUENCE: 8
caagggcccc tccttttgcg gcaatctcac tgacgag                                37

<210> SEQ ID NO 9
<211> LENGTH: 35
<212> TYPE: DNA
<213> ORGANISM: Homo sapiens

<400> SEQUENCE: 9
gcccctactg ggccgccgca tgttacaccc taaag                                  35

<210> SEQ ID NO 10
<211> LENGTH: 35
```

-continued

```
<212> TYPE: DNA
<213> ORGANISM: Homo sapiens

<400> SEQUENCE: 10
ctttagggtg taacatgcgg cggcccagta ggggc                               35

<210> SEQ ID NO 11
<211> LENGTH: 39
<212> TYPE: DNA
<213> ORGANISM: Homo sapiens

<400> SEQUENCE: 11
gtcagtgaga ttcccccagc aggaggggcc cttggggag                           39

<210> SEQ ID NO 12
<211> LENGTH: 39
<212> TYPE: DNA
<213> ORGANISM: Homo sapiens

<400> SEQUENCE: 12
ctccccaagg gcccctcctg ctgggggaat ctcactgac                           39

<210> SEQ ID NO 13
<211> LENGTH: 33
<212> TYPE: DNA
<213> ORGANISM: Homo sapiens

<400> SEQUENCE: 13
ggaggggccc ttgggggcggg gcctggggcc tcc                                33

<210> SEQ ID NO 14
<211> LENGTH: 33
<212> TYPE: DNA
<213> ORGANISM: Homo sapiens

<400> SEQUENCE: 14
ggaggcccca ggccccgccc caagggcccc tcc                                 33

<210> SEQ ID NO 15
<211> LENGTH: 33
<212> TYPE: DNA
<213> ORGANISM: Homo sapiens

<400> SEQUENCE: 15
cagcatagcc cctacgcggc cccccatgt tac                                  33

<210> SEQ ID NO 16
<211> LENGTH: 33
<212> TYPE: DNA
<213> ORGANISM: HOMO SAPIENS

<400> SEQUENCE: 16
gtaacatggg ggggccgcgt agggctatg ctg                                  33

<210> SEQ ID NO 17
<211> LENGTH: 44
<212> TYPE: PRT
<213> ORGANISM: Homo sapiens

<400> SEQUENCE: 17

Trp Leu Glu Arg Thr Met Pro Arg Ile Pro Thr Leu Lys Asn Leu Glu
1               5                   10                  15

Asp Leu Val Thr Glu Tyr His Gly Asn Phe Ser Ala Trp Ser Gly Val
            20                  25                  30
```

-continued

Ser Lys Gly Leu Ala Glu Ser Leu Gln Pro Asp Tyr
        35                  40

<210> SEQ ID NO 18
<211> LENGTH: 81
<212> TYPE: PRT
<213> ORGANISM: Homo sapiens

<400> SEQUENCE: 18

His Arg Val Ser Ala Ala Glu Leu Gly Gly Lys Val Asn Arg Ala Leu
1               5                   10                  15

Gln Gln Val Gly Gly Leu Lys Ser Pro Trp Arg Gly Glu Tyr Lys Glu
            20                  25                  30

Pro Arg His Pro Pro Asn Gln Ala Asn Tyr His Gln Thr Leu His
        35                  40                  45

Ala Gln Pro Arg Glu Leu Ser Pro Arg Ala Pro Gly Pro Arg Pro Ala
    50                  55                  60

Glu Glu Thr Thr Gly Arg Ala Pro Lys Leu Gln Pro Pro Leu Pro Pro
65                  70                  75                  80

Glu

<210> SEQ ID NO 19
<211> LENGTH: 324
<212> TYPE: PRT
<213> ORGANISM: Homo sapiens

<400> SEQUENCE: 19

Pro Leu Thr Ala Gln Ala Ile Gln Glu Gly Leu Arg Lys Glu Pro Ile
1               5                   10                  15

His Arg Val Ser Ala Ala Glu Leu Gly Gly Lys Val Asn Arg Ala Leu
            20                  25                  30

Gln Gln Val Gly Gly Leu Lys Ser Pro Trp Arg Gly Glu Tyr Lys Glu
        35                  40                  45

Pro Arg His Pro Pro Asn Gln Ala Asn Tyr His Gln Thr Leu His
    50                  55                  60

Ala Gln Pro Arg Glu Leu Ser Pro Arg Ala Pro Gly Pro Arg Pro Ala
65                  70                  75                  80

Glu Glu Thr Thr Gly Arg Ala Pro Lys Leu Gln Pro Pro Leu Pro Pro
                85                  90                  95

Glu Pro Pro Glu Pro Asn Lys Ser Pro Pro Leu Thr Leu Ser Lys Glu
            100                 105                 110

Glu Ser Gly Met Trp Glu Pro Leu Pro Leu Ser Ser Leu Glu Pro Ala
        115                 120                 125

Pro Ala Arg Asn Pro Ser Ser Pro Glu Arg Lys Ala Thr Val Pro Glu
    130                 135                 140

Gln Glu Leu Gln Gln Leu Glu Ile Glu Leu Phe Leu Asn Ser Leu Ser
145                 150                 155                 160

Gln Pro Phe Ser Leu Glu Glu Gln Gln Ile Leu Ser Cys Leu Ser
                165                 170                 175

Ile Asp Ser Leu Ser Leu Ser Asp Asp Ser Glu Lys Asn Pro Ser Lys
            180                 185                 190

Ala Ser Gln Ser Ser Arg Asp Thr Leu Ser Ser Gly Val His Ser Trp
        195                 200                 205

Ser Ser Gln Ala Glu Ala Arg Ser Ser Ser Trp Asn Met Val Leu Ala
    210                 215                 220

Arg Gly Arg Pro Thr Asp Thr Pro Ser Tyr Phe Asn Gly Val Lys Val

-continued

```
            225                 230                 235                     240
Gln Ile Gln Ser Leu Asn Gly Glu His Leu His Ile Arg Glu Phe His
                    245                 250                 255

Arg Val Lys Val Gly Asp Ile Ala Thr Gly Ile Ser Ser Gln Ile Pro
            260                 265                 270

Ala Ala Ala Phe Ser Leu Val Thr Lys Asp Gly Gln Pro Val Arg Tyr
            275                 280                 285

Asp Met Glu Val Pro Asp Ser Gly Ile Asp Leu Gln Cys Thr Leu Ala
        290                 295                 300

Pro Asp Gly Ser Phe Ala Trp Ser Trp Arg Val Lys His Gly Gln Leu
305                 310                 315                 320

Glu Asn Arg Pro
```

DERIVATIVES OF THE NF-κB INDUCING ENZYME, THEIR PREPARATION AND USE

FIELD OF THE INVENTION

This invention relates to the use of NIK and related molecules for the modulation of signal activities controlled by cytokines, and some new such molecules.

BACKGROUND OF THE INVENTION

Nuclear factor κB (NF-κB) is a family of inducible eukaryotic transcription factor complexes participating in regulation of immune response, cell growth, and survival [Ghosh et al. 1998]. The NF-κB factors are normally sequestered in the cytoplasmic compartment by physical association with a family of cytoplasmic ankyrin rich inhibitors termed IκB, including IκBα and related proteins [Baldwin et al. 1996]. In response to diverse stimuli, including cytokines, mitogens, and certain viral gene products, IκB is rapidly phosphorylated at serines 32 and 36, ubiquitinated and then degraded by the 26S proteasome, which allows the liberated NF-κB to translocate to the nucleus and participate in target gene transactivation [Mercurio et al 1999, Pahl et al 1999]. Recent molecular cloning studies have identified a multi subunit IκB kinase (IKK) that mediates the signal-induced phosphorylation of IκB. The IKK is composed of two catalytic subunits, IKKα and IKMβ, and a regulatory subunit IKKγ. The catalytic activity of both IKKα and IKKβ can be activated by a multitude of different NF-κB inducers, including the inflammatory cytokines, tumor necrosis factor and interleukin-1, the T cell receptor and the T cell costimulatory protein, CD28 [Karin et al 2000].

NF-κB-inducing kinase, NIK, (MAP3K14) is a mitogen activated protein kinase (MAP3K) that was discovered by applicants in 1996 (WO9737016) while screening for proteins that bind to the TNF-receptor associated adaptor protein TRAF2 [Rothe et al. 1994, Takeuchi et al. 1996]. Marked activation of NF-κB upon overexpression of this protein kinase, and effective inhibition of NF-κB activation in response to a variety of inducing agents (LMP1, TNFR1, TNFR2, RANK, hTollR, CD3/CD28, interleukin-1R, human T-cell lymphotropic virus-1 Tax, LPS and others [Mlinin et al. 1997, Sylla et al 1998, Darnay et al. 1999, Lin et al. 1999, Geleziunas et al. 1998] upon expression of catalytically inactive NIK mutants suggested that NIK participates in signaling for NF-κB activation [Mlinin et al. 1997].

Targeted disruption of the NIK gene [Yin et al 2001] and study of a naturally occurring mice strain with a point missense mutation in NIK (glycine to arginine at mNIK codon 855) [Shinkaura et al. 1999] revealed an essential role of NIK in lymphoid organ development, thus the mice mutant strain has been called 'alymphoplasia (aly)' mice. Both the aly/aly and NIK knockout mice manifest systemic absence of lymph nodes and Peyer's patches, disorganized splenic and thymic architectures, and immunodeficiency whose most resilient features are low serum Ig levels and lack of graft rejection [Shinkaura et al. 1999]. These abnormalities apparently reflect aberrant signaling by a variety of receptors. The developmental deficiencies of the NIK mutant mice resemble those found in mice deficient in the LTβ receptor (LTβR) suggesting that NIK participates in signaling by this particular receptor. Impaired B cell proliferative capacity in the aly/aly mice could be shown to correlate to a deficient response of these cells to LPS and CD40L [Garceau et al. 2000], and presence of excessive amounts of B1 cells in the mice peritoneal cavity could be ascribed to defects in homing of peritoneal cells to the gut associated lymphatic tissue system as a consequence of deficient chemokine receptor signaling in the secondary lymphoid tissue [Fagarasan et al. 2000].

Apart from these and probably other contributions to the regulation of the development and function of the immune system, NIK seems also to be involved in the regulation of various non-immune functions. The aly/aly (though not the NIK knockout) mice display deficient mammary gland development [Miyawaki 1994]. Moreover, in vitro studies implicated NIK in signaling that leads to skeletal muscle cell differentiation [Canicio et al. 2001] and in the survival and differentiation of neurons [Foher et al 2000].

Consistent with the suggested role of NIK as mediator of NF-κB activation, fibroblasts derived from aly/aly and NIK–/– mice fail to activate NF-κB in response to LTβR activation. Moreover, LTβR upregulation of VCAM-1, which occurs through NF-κB activation, is abnormal in aly/aly murine embryonic fibroblasts [Matsumoto et al. 1999]. Deficient phosphorylation of IκB has also been noted in the response of aly/aly B-lymphocytes to CD40 ligation. In contrast, in dendritic cells of these mice CD40-induced phosphorylation of IκB appeared normal [Garceau et al 1998]. Aly/aly peritoneal cells are also incapable of responding to the chemokine SLC with increased NF-κB activity [Fagarasan et al. 2000] However, in none of the cells examined so far was the effect of TNF or IL-1 on NF-κB activation found to be ablated by NIK mutation.

Assessment of the pattern of the NF-κB species in lymphoid organs of aly/aly mice indicated that, apart from its role in the regulation of NF-κB complex(s) comprised of Rel proteins (A+p50) and IκB, NIK also participates in controlling the expression/activation of other NF-κB species. Most notably, the lymphocytes of the aly/aly mice were deficient of p52, an NF-κB species that is specifically formed in mature B-lymphocytes through proteolytic processing of an inactive precursor, p100 (NF-κB2), suggesting a deficiency in p100-p52 conversion [Yamada et al. 2000]. Indeed, NIK has been shown to participate in site specific phosphorylation of p100, both directly and through phosphorylation of IKKα, which in turn phosphorylates p100. This phosphorylation serves as a molecular trigger for ubiquitination and active processing of p100 to form p52. This p100 processing activity was found to be ablated by the aly mutation [Xiao et al. 2001, Senftleben et al. 2001].

In view of the structural homology of NIK to MAP3Ks, some attempts have been made to explore the involvement of NIK in the three other main protein kinase cascades known to involve MAP3Ks (the MAP kinase cascades: the ERK, JNK and p38 cascades)[Akiba et al. 1998]. Though in certain cells NIK seems not to participate in any of these cascades, some others cells (PC12) do appear to involve NIK in the ERK cascade [Fochr et al. 2000]. Evidence has also been presented that in certain cells NIK may participate in signaling to the phosphorylation of Jun, the downstream target of the JNK cascade, in a way that is independent of this particular cascade [Akiba et al. 1998, Natoli et al. 1997]. In all, these findings indicate that NIK indeed serves as a mediator of NF-κB activation, but may also serve other functions, and that it exerts these functions in a cell- and receptor-specific manner.

Like other MAP3Ks, NIK can be activated as a consequence of phosphorylation of the 'activation loop' within the NIK molecule. Indeed, mutation of a phosphorylation-site within this loop (Thr-559) prevents activation of NF-κB upon NIK overexpression [Lin et al. 1999]. In addition, the activity of NIK seems to be regulated through the ability of the regions upstream and downstream of its kinase motif to bind to each other. The C-terminal region of NIK downstream of its kinase moiety has been shown to be capable of binding directly to IKKα [Regnier et al. 1997]as well as to p100 [Xiao et al. 2001] and to TRAF2 [Malinin et al. 1997]. These interactions are apparently required for NIK function in NF-κB signaling. The N-terminal region of NIK contains a negative-regulatory domain (NRD), which is composed of a basic motif (BR) and a proline-rich repeat motif (PRR) [Xiao et al. 2000]. Apparently, the N-terminal NRD interacts with the C-terminal region of NIK in cis, thereby inhibiting the binding of NIK to its substrate (IKKα and p100). Ectopically expressed NIK seems to spontaneously form oligomers in which these bindings of the N-terminal to the C-terminal regions in each NIK molecule are apparently disrupted, and display a high level of constitutive activity [Lin et al. 1999]. The binding of the NIK C-terminal region to TRAF2 (as well as to other TRAF's) most likely participates in the activation process of NIK. However, its exact mode of participation is unknown.

There is likewise rather limited information yet of the downstream mechanisms in NIK action. Evidence has been presented that NIK, through the binding of its C-terminal region to IKKα can activate the IκB kinase (IKK) complex. It has indeed been shown to be capable of phosphorylating serine-176 in the activation loop of IKKα, thereby activating IKKα [Ling et al. 1998]. Consistent with such mode of action, studies of the mechanisms accounting for the deficient activation of NF-κB by the LTβR in aly/aly mice murine embryonic fibroblasts (MEF's) indicated that NIK mutation ablates activation of the IKK signalosome and the consequent phosphorylation of IκB [Matsushima et al 2001]. These findings were not supported, however, by the analysis of MEF's derived from NIK -/- mice. Although the NIK deficient MEF's are unable to manifest NF-κB activation in response to LTβ, they do seem to respond normally to it in terms of IκB phosphorylation and degradation [Yin et al. 2001]. According to these findings, NIK may not participate at all in the activation of the IKK complex by the LTβR but is rather involved by an as yet unknown mechanism in controlling the transcriptional action of the NF-κB complex after its translocation to the nucleus. There are also still uncertainties as to the way by which NIK triggers p100 phosphorylation and processing. Its ability to bind p100 directly through its C-terminal region and phosphorylate it suggests that p100 serves as a direct NIK substrate [Xiao et al. 2000]. Nevertheless, a recent study has suggested that NIK mediates p100 phosphorylation in an indirect way, through phosphorylation and thus activation of IKKα that in turn phosphorylates p100 [Senftleben et al.2001].

Yamamoto and Gaynor reviewed the role of NF-κB in pathogenesis of human disease (Yamamoto and Gaynor 2001). Activation of the NF-κB pathway is involved in the pathogenesis of chronic inflammatory disease, such as asthma, rheumatoid arthritis (see Tak and Firestein, this Perspective series, ref. Karin et al. 2000), and inflammatory bowel disease. In addition, altered NF-κB regulation may be involved in other diseases such as atherosclerosis (see Collins and Cybulsky, this series, ref. Leonard et al. 1995) and Alzheimer's disease (see Mattson and Camandola, this series, ref Lin et al. 1999), in which the inflammatory response is at least partially involved. Finally, abnormalities in the NF-κB pathway are also frequently seen in a variety of human cancers.

Several lines of evidence suggest that NF-κB activation of cytokine genes is an important contributor to the pathogenesis of asthma, which is characterized by the infiltration of inflammatory cells and the deregulation of many cytokines and chemokines in the lung (Ling et al. 1998). Likewise, activation of the NF-κB pathway also likely plays a role in the pathogenesis of rheumatoid arthritis. Cytokines, such as TNF-α, that activate NF-κB are elevated in the synovial fluid of patients with rheumatoid arthritis and contribute to the chronic inflammatory changes and synovial hyperplasia seen in the joints of these patients (Malinin et al. 1997). The administration of antibodies directed against TNF-α or a truncated TNF-α receptor that binds to TNF-α can markedly improve the symptoms of patients with rheumatoid arthritis.

Increases in the production of proinflammatory cytokines by both lymphocytes and macrophages have also been implicated in the pathogenesis of inflammatory bowel diseases, including Crohn's disease and ulcerative colitis (Matsumoto et al. 1999). NF-κB activation is seen in mucosal biopsy specimens from patients with active Crohn's disease and ulcerative colitis. Treatment of patients with inflammatory bowel diseases with steroids decreases NF-κB activity in biopsy specimens and reduces clinical symptoms. These results suggest that stimulation of the NF-κB pathway may be involved in the enhanced inflammatory response associated with these diseases.

Atherosclerosis is triggered by numerous insults to the endothelium and smooth muscle of the damaged vessel wall (Matsushima et al. 2001). A large number of growth factors, cytokines, and chemokines released from endothelial cells, smooth muscle, macrophages, and lymphocytes are involved in this chronic inflammatory and fibroproliferative process (Matsushima et al. 2001). NF-κB regulation of genes involved in the inflammatory response and in the control of cellular proliferation likely plays an important role in the initiation and progression of atherosclerosis.

Finally, abnormalities in the regulation of the NF-κB pathway may be involved in the pathogenesis of Alzheimer's disease. For example, NF-κB immunoreactivity is found predominantly in and around early neuritic plaque types in Alzheimer's disease, whereas mature plaque types show vastly reduced NF-κB activity (Mercurio et al. 1999). Thus, NF-κB activation may be involved in the initiation of neuritic plaques and neuronal apoptosis during the early phases of Alzheimer's disease. These data suggest that activation of the NF-κB pathway may play a role in a number of diseases that have an inflammatory component involved in their pathogenesis.

In addition to a role in the pathogenesis of diseases characterized by increases in the host immune and inflammatory response, constitutive activation of the NF-κB pathway has also been implicated in the pathogenesis of some human cancers. Abnormalities in the regulation of the NF-κB pathway are frequently seen in a variety of human malignancies including leukemias, lymphomas, and solid tumors (Miyawaki et al. 1994). These abnormalities result in constitutively high levels of NF-κB in the nucleus of a variety of tumors including breast, ovarian, prostate, and colon cancers. The majority of these changes are likely due to alterations in regulatory proteins that activate signaling pathways that lead to activation of the NF-κB pathway. However, mutations that inactivate the IκB proteins in addition to amplification and rearrangements of genes encoding NF-κB family members can result in the enhanced nuclear levels of NF-κB seen in some tumors.

IL2 is a protein of 133 amino acids (15.4 kDa) with a slightly basic pI. It does not display sequence homology to any other factors. Murine and human IL2 display a homology of approximately 65 percent. IL2 is synthesized as a precursor protein of 153 amino acids with the first 20 aminoterminal amino acids functioning as a hydrophobic secretory signal sequence. The protein contains a single disulfide bond (positions Cys58/105) essential for biological activity.

Mouse and human IL2 both cause proliferation of T-cells of the homologous species at high efficiency. Human IL2 also stimulates proliferation of mouse T-cells at similar concentrations, whereas mouse IL2 stimulates human T-cells at a lower (sixfold to 170-fold) efficiency. The involvement of IL-2 in autoimmunity is controversial (reviewed by O'Shea et al. 2002) It is recognized that IL-2 administration is associated with a variety of autoimmune disorders such as immune thyroiditis, rheumatoid arthritis and other arthropathies. However IL-2 deficient mice produce multiple autoantibodies, including anti-DNA antibodies. About half die of autoimmune haemolytic anemia and the survivors develop inflammatory bowel disease. Importantly, the pathology is corrected by the addition of exogenous IL-2. This indicates a role of IL-2 in maintaining peripheral tolerance.

IL2 is a growth factor for all subpopulations of T-lymphocytes. The IL2R-alpha receptor subunit is expressed in adult T-cell leukemia (ATL). Since freshly isolated leukemic cells also secrete IL2 and respond to it, IL2 may function as an autocrine growth modulator for these cells capable of worsening ATL.

IL2 also promotes the proliferation of activated B-cells. Such activity requires the presence of additional factors, for example, IL-4. In vitro IL-2 also stimulates the growth of oligodendroglial cells.

Therefore, due to its effects on T-cells and B-cells IL-2 is a central regulator of immune responses. It also plays a role in anti-inflammatory reactions in hematopoiesis and in tumor surveillance. IL2 stimulates the synthesis of IFN-gamma in peripheral leukocytes and also induces the secretion IL-1 TNF-alpha and TNF-beta.

The biological activities of IL2 are mediated by a membrane receptor. Three different types of IL2 receptors are distinguished that are expressed differentially and independently. The high affinity IL2 receptor constitutes approximately 10 percent of all IL2 receptors expressed by cells. This receptor is a membrane receptor complex consisting of the two subunits IL2R-alpha and IL2R-beta as the ligand binding domains and a gamma chain as a signaling component. IL2R-beta is expressed constitutively on resting T-lymphocytes, NK-cells, and a number of other cell types while the expression of IL-2R-alpha is usually observed only after cell activation. IL-2-alpha is, however, synthesized constitutively by a number of tumor cells and by HTLV-1-infected cells.

IL2 receptor expression of monocytes is induced by IFNγ so that these cells become tumor-cytotoxic.

Murine and human gamma subunits of the receptor have approximately 70 percent sequence identity at the nucleotide and amino acid levels. This subunit is required for the generation of high and intermediate affinity IL2 receptors but does not bind IL2 by itself. These two receptor types consist of an alpha-beta-gamma heterotrimer and a beta-gamma heterodimer, respectively. The gene encoding the gamma subunit of the IL2 receptor maps to human chromosome Xq13, spans approximately 4.2 kb and contains eight exons. Relationships to markers in linkage studies suggest that this gene and SCIDX1, the gene for X-linked severe combined immunodeficiency, have the same location. Moreover, in each of 3 unrelated patients with X-linked SCID, a different mutation in the IL2R-gamma gene has been observed.

X-linked severe combined immunodeficiency (XSCID) is a rare and potentially fatal disease caused by mutations of IL2Rγchain, the gene encoding the IL-2R γ chain, a component of multiple cytokine receptors that are essential for lymphocyte development and function (Noguchi et al. 1993). To date, over 100 different mutations of IL2RG resulting in XSCID have been published. Recent gene knock out studies indicate a pivotal role of this gene in lymphopoiesis [DiSanto et al 1995].

The IL-2Rγ chain is a subunit of the IL-2, IL-4, IL-7, IL-9, IL-13, IL-15 and IL-21 receptor complexes wherefore it now dubbed as the 'common γ chain' (cγc).

EP0578932 relates to the whole common gamma chain and especially to the extracellular N-terminal domain.

Consistent with the involvement of IL-2 in autoimmunity there exists a need for a modulator of IL-2 activity for preventing or alleviating said diseases.

SUMMARY OF THE INVENTION

The present invention relates to the use of NIK or a mutein, variant, fusion protein, functional derivative, circularly permutated derivative or fragment thereof, preferably the fragments comprised in SEQ ID NO:19, SEQID NO: 18, and the mutant AlyNIK, for modulating the interaction between IL-2 receptor gamma chain (also known as common gamma chain) (cγc) and NIK and preferably to the fragments comprised in SEQ ID NO:19, SEQ ID NO: 18, and to the mutant AlyNIK.

In addition the invention relates to the use of a DNA encoding NIK according to the invention or its antisense, NIK specific antibodies, a small molecule obtainable by screening products of combinatorial chemistry in a luciferase system, for modulating the interaction between common gamma chain (cγc) and NIK.

In another aspect, the present invention relates to the use of NIK or a mutein, variant, fusion protein, functional derivative, circularly permutated derivative or fragment thereof, preferably the fragments comprised in SEQ ID NO:19, SEQ ID NO: 18, and the mutant AlyNIK, in the manufacture of a medicament for the treatment of a disease, wherein a cytokine stimulating signalling through the cγc is involved in the pathogenesis of the disease.

In addition the invention relates to the use of a DNA encoding NIK according to the invention or its antisense, NIK specific antibodies, a small molecule obtainable by screening products of combinatorial chemistry in a luciferase system, for the treatment of a disease, wherein a cytokine stimulating signalling through the cγc is involved in the pathogenesis of the disease, for inhibiting signalling through cγc.

The invention also provides methods for the treatment of a disease involving signalling of a cytokine through cγc in the pathogenesis of said disease, particularly IL-2 or IL-15, comprising administration of a therapeutically effective amount of NIK or a mutein, variant, fusion protein, functional derivative, circularly permutated derivative or fragment thereof, preferably the fragments comprised in SEQ ID NO:19, SEQ ID NO: 18, and the mutant AlyNIK, in a subject in need.

In addition the invention relates methods for the treatment of a disease involving signalling of a cytokine through cγc in the pathogenesis of said disease comprising administration of a therapeutically effective amount of DNA encoding NIK according to the invention or its antisense, NIK specific antibodies or a small molecule obtainable by screening products of combinatorial chemistry in a luciferase system.

Moreover, the present invention relates to a pharmaceutical composition comprising NIK or a mutein, variant, fusion protein, functional derivative, circularly permutated derivative or fragment thereof, preferably the fragments comprised in SEQ ID NO:19, SEQ ID NO: 18, and the mutant AlyNIK, for modulating the interaction between common gamma chain (cγc) and NIK, wherein a cytokine stimulating cγc signalling is involved in the pathogenesis of the disease, a cytokine stimulating signalling through cγc is involved in the pathogenesis of the disease or the interaction between cγc and NIK is involved in the pathogenesis of a disease.

In addition the invention relates to a pharmaceutical composition comprising a DNA encoding NIK according to the invention or its antisense, NIK specific antibodies or a small molecule obtainable by screening products of combinatorial chemistry in a luciferase system, for the treatment of a disease, wherein a cytokine stimulating signalling through the cγc is involved in the pathogenesis of the disease, for modulating the interaction between common gamma chain (cγc) and NIK, wherein a cytokine stimulating cγc signalling is involved in the pathogenesis of the disease, a cytokine stimulating signalling through cγc is involved in the pathogenesis of the disease or the interaction between cγc and NIK is involved in the pathogenesis of a disease.

In another aspect, the present invention relates to a polypeptide fragment of NIK, comprising the common gamma chain (cγc) binding domain, or a mutein, variant, fusion protein, functional derivative, circularly permutated derivative or fragment thereof, preferably the fragments comprised in SEQ ID NO:19, SEQ ID NO: 18, and the mutant AlyNIK, for modulating the interaction between common gamma chain (cγc) and NIK and preferably to the fragments comprised in SEQ ID NO:19, SEQ ID NO: 18, and to the mutant AlyNIK, a DNA encoding the polypeptides of the invention, a vector comprising the DNA, host cells comprising the vector and a method for the production of a NIK polypeptide fragment according to the invention the cell of the invention and collecting the polypeptide produced.

Furthermore, the present invention provides antibodies, polyclonal or monoclonal, chimeric antibody, fully humanized antibody, anti-anti-Id antibody, intrabody or fragment thereof which specifically recognises and binds the polypeptide fragment of NIK of the invention and a small molecule able to inhibit NIK-cγc interaction obtainable by screening of molecules prepared by combinatory chemistry in a luciferase system.

In addition the invention relates to a pharmaceutical composition comprising a polypeptide fragment of NIK, preferably the fragments comprised in SEQ ID NO:19, and in SEQ ID NO: 18, DNA encoding the fragments or antisense DNA, a vector comprising the DNA, antibodies of the invention or the small molecule able to inhibit NIK-cγc interaction obtainable by screening of molecules prepared by combinatory chemistry in a luciferase system.

In one embodiment the pharmaceutical is provided for the treatment of a disease wherein NIK and cγc interaction is involved in the pathogenesis of said disease while in another embodiment the pharmaceutical is provided for the treatment of a disease wherein the activity of a cytokine having the common gamma chain in its receptor, such as IL-2 and IL-15, is involved in the pathogenesis of the disease.

The invention also provides the use of a polypeptide fragment of NIK of the invention, in the manufacture of a medicament for treatment of a disease, wherein the activity of a cytokine having the common gamma chain in its receptor, such as IL-2 and IL-15, or wherein NIK and cγc interaction is involved in the pathogenesis of said disease.

In another aspect the invention provides the use of a fragment of NIK, comprising the cγc binding domain (SEQ ID NO: 18), or a mutein, variant, fusion protein, functional derivative, circularly permutated derivative or fragment thereof, in the manufacture of a medicament for the treatment and/or prevention of a disease resulting from excessive immune responses, such as rheumatoid arthritis, osteoarthritis, inflammatory bowel disease, asthma, cardiac infarct, Alzheimer's disease, or atherosclerosis.

In another aspect the invention provides the use of a fragment of NIK, comprising the cγc binding domain (SEQ ID NO: 18), or a mutein, variant, fusion protein, functional derivative, circularly permutated derivative or fragment thereof, in the manufacture of a medicament for the treatment and/or prevention of autoimmune diseases, such as thyroiditis, rheumatoid arthritis and other arthropaties, autoimmune haemolytic anemia and inflammatory bowel disease.

In addition, the invetion provides a method for the treatment and/or prevention of a disease in which activation of a cytokine, having the common gamma chain in its receptor (such as IL-2 and IL-15), is involved in the pathogenesis of the disease, comprising administering a therapeutically effective amount of a polypeptide fragment of NIK, comprising the cγc binding domain (SEQ ID NO: 18), or a mutein, variant, fusion protein, functional derivative, circularly permutated derivative or fragment thereof to a subject in need.

In a further embodiment, the invention provides a method of treatment and/or prevention of a disease in which NF-κB activation is involved, such as cancer rheumatoid arthritis, osteoarthritis, inflammatory bowel disease, asthma, cardiac infarct, Alzheimer's disease, or atherosclerosis, and comprising administering to a host in need thereof an effective amount of a fragment of NIK, corresponding to the cγc binding domain (SEQ ID NO: 18), or a mutein, variant, fusion protein, functional derivative, circularly permutated derivative or fragment thereof.

In addition the invention provides a method of treatment and/or prevention of a disease resulting from excessive immune responses, such as rheumatoid arthritis, osteoarthritis, inflammatory bowel disease, asthma, cardiac infarct, Alzheimer's disease, or atherosclerosis, comprising administering to a host in need thereof a therapeutically effective amount of a polypeptide comprising a fragment of NIK, corresponding to the cγc binding domain (SEQ ID NO: 18), or a mutein, variant, fusion protein, functional derivative, circularly permutated derivative or fragment thereof.

3—lysate of cells transfected with pcS3MTNIK immunoprecipitated with anti NIK. 2—lysate of cells transfected with pcS3MTNIK and immunoprecipitated with anti cγc antibody. 1—lysates of cells transfected with both pcS3MTNIK and pcDNA3cγc and immunoprecipitated with anti cγc antibody. 5—lysate of non-transfected cells. 4 and 6—lysates of cells transfected with both pcS3MTNIK and pcDNA3cγc or cells transfected with pcS3MTNIK alone, respectively, before immunoprecipitation.

Figure 4:
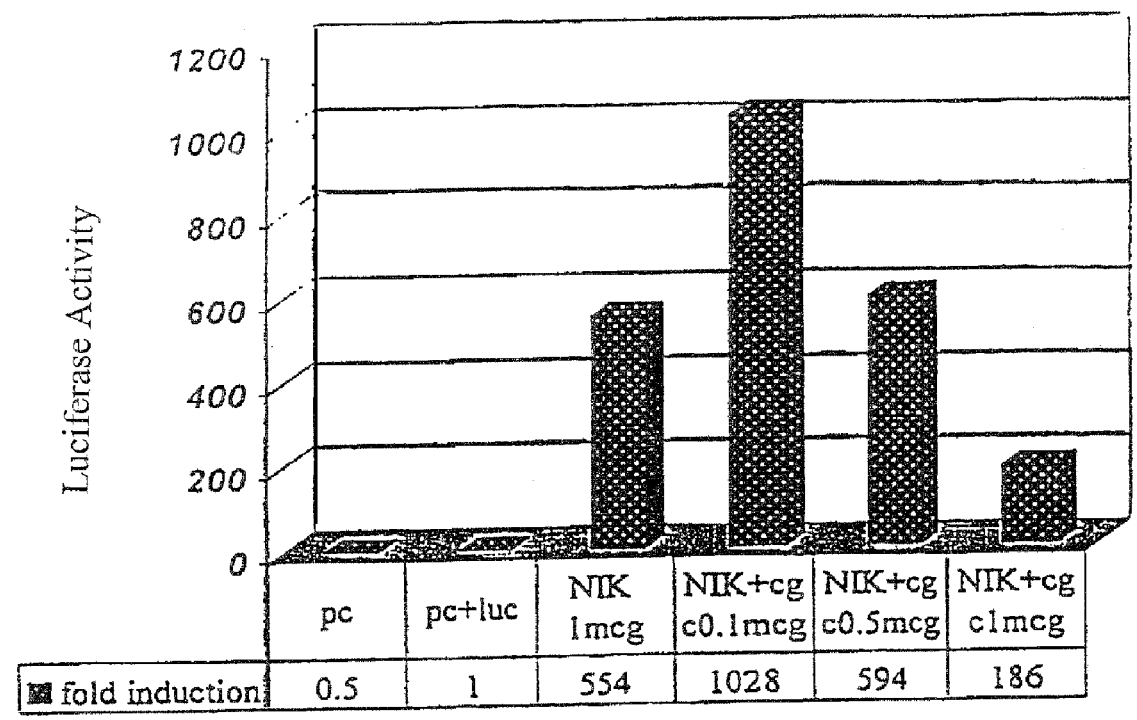

FIG. 4 shows the concentration-dependent effect of cγc on NIK induced NF-κB activation. Activation of NF-κB is monitored by the luciferase reporter assay (for details see Example 10). NF-κB activation in 293-T cells was induced by overexpressing NIK. Luciferase expression was monitored in cells transfected with the following plasmids: empty plasmid (sample pc), empty plasmid and a plasmid encoding luciferase under the control of an NF-κB inducible promoter (pcDNA3luciferase, 0.5 μg/well) (sample pc+luc), 1 μg pcS3MTNIK and pcDNA3luciferase (sample NIK 1 mcg), 1 μg pcS3MTNIK, 0.1 μg/well pcDNA3cγc and pcDNA3luciferase (sample NIK+cgc 0.1 mcg), 1 μg pcS3MTNIK, 0.5 μg/well pcDNA3cγc and pcDNA3luciferase (sample NIK+cgc 0.5 mcg), and 1 μg pcS3MTNIK with 1 μg/well pcDNA3cγc and pcDNA3luciferase (sample NIK+cgc 1 mcg).

Figure 5:
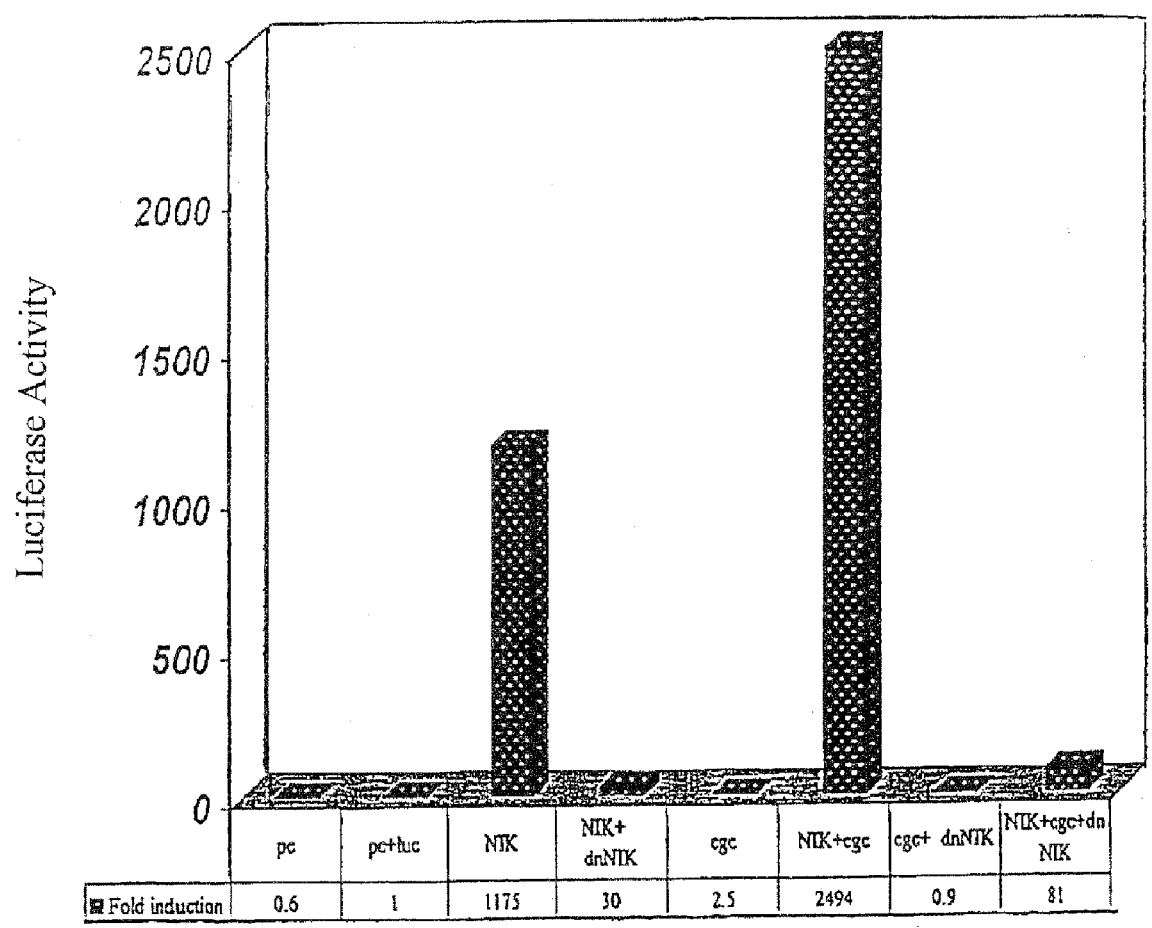

FIG. 5 shows the effect of a dominant negative mutant of NIK (dnNIK, residues 624-947) on cγc enhanced NF-κB activation. Activation of NF-κB is monitored by the luciferase reporter assay (for details see Example 10). NF-κB activation in 293-T cells was induced by overexpressing NIK. Luciferase expression was monitored in cells transfected with the following plasmids: empty plasmid (sample pc), empty plasmid and a plasmid encoding luciferase under the control of an NF-κB inducible promoter (pcDNA3luciferase) (sample pc+luc), pcS3MTNIK and pcDNA3luciferase (sample NIK), pcS3MTNIK, pcS3MTdnNIK and pcDNA3luciferase (sample NIK+dnNIK) pcDNA3cγc and pcDNA3luciferase (sample cgc), pcS3MTNIK, pcDNA3cγc and pcDNA3luciferase (sample NIK+cgc), pcS3MTdnNIK, pcDNA3cγc and pcDNA3luciferase (sample cgc+dnNIK), pcS3MTNIK, pcDNA3cγc, pcS3MTdnNIK and pcDNA3luciferase (sample NIK+cgc+dnNIK). pcS3MTdnNIK, pcS3MTNIK and pcDNA3cγc were used at a concentration of 1, 1, and 0.1 μg/well respectively.

Figure 6:
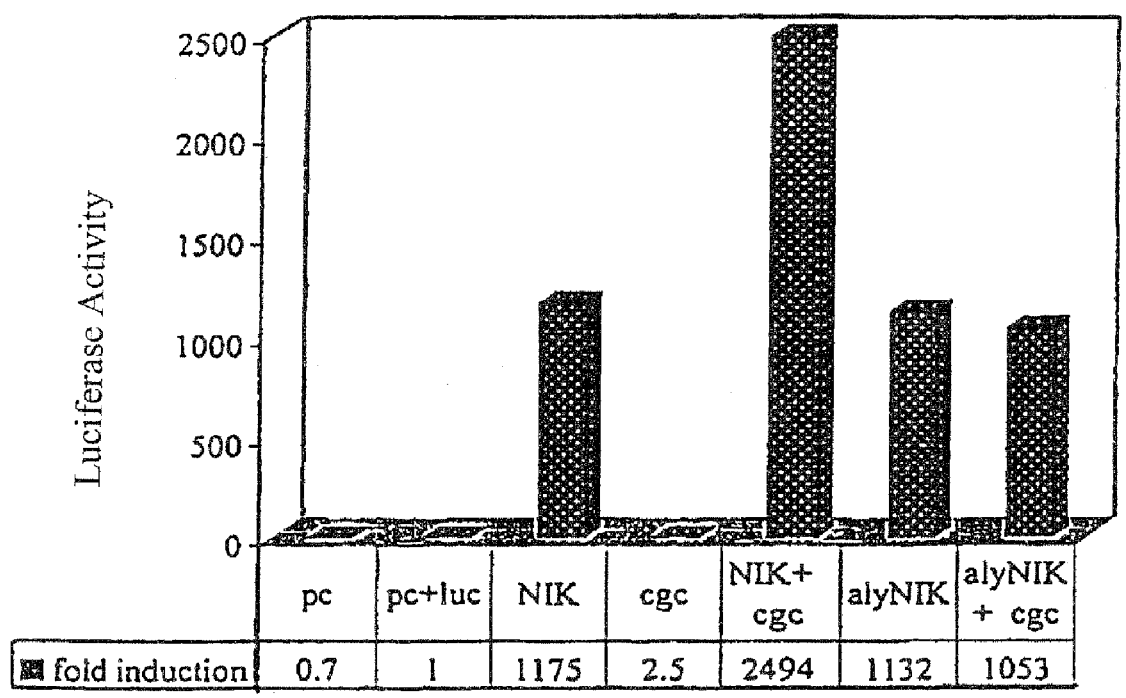

FIG. 6 shows the effect of cγc on NF-κB activation induced by the NIKaly mutant. Activation of NF-κB is monitored by the luciferase reporter assay (for details see Example 10). NF-κB activation in cells is induced by overexpressing NIK. Luciferase expression was monitored in 293-T cells transfected with the following plasmids: empty plasmid (sample pc), empty plasmid and a plasmid encoding luciferase under the control of an NF-κB inducible promoter (pcDNA3luciferase) (sample pc+luc), pcS3MTNIK and pcDNA3luciferase (sample NIK), pcDNA3luciferase and pcDNA3cγc (sample cγc), pcS3MTNIK, pcDNA3cγc and pcDNA3luciferase (sample NIK+cgc), 1μg pcS3MTAlyNIK and pcDNA3luciferase (sample AlyNIK) and pcS3MTAlyNIK, pcDNA3cγc and pcDNA3luciferase (sample AlyNIK+cgc). pcS3MT AlyNIKNIK, pcS3MTNIK and pcDNA3cγc were used at a concentration of 1, 1, and 0.1 μg/well respectively.

Figure 7:
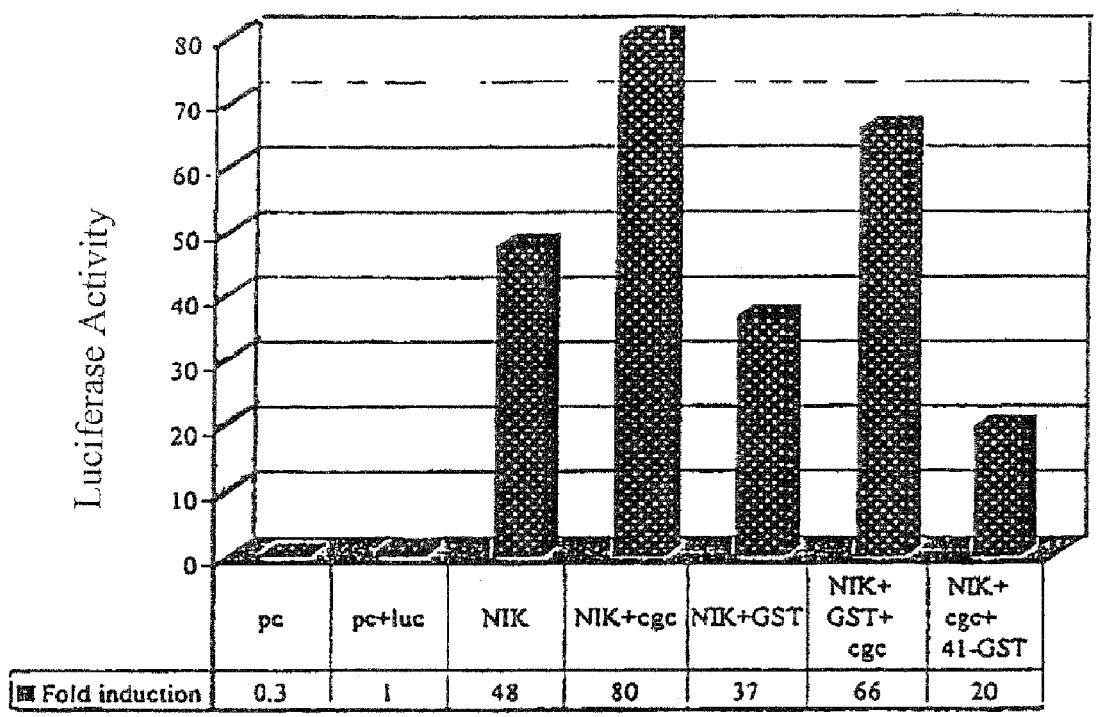

FIG. 7 shows the effect of a 41 amino acid polypeptide derived from the membrane distal end of cγc (41MDD) on NIK induced NF-κB activation and enhancement by full-length cγc. Activation of NF-κB is monitored by the luciferase reporter assay (for details see Example 10). NF-κB activation in 293-T cells was induced by overexpressing NIK. Enhancement of NF-κB induction is obtained by overexpressing NIK and expressing the full cγc at low concentration. Luciferase expression was monitored in cells transfected with the following plasmids: empty plasmid (sample pc), empty plasmid and a plasmid encoding luciferase under the control of an NF-κB inducible promoter (pcDNA3luciferase) (sample pc+luc), pcS3MTNIK and pcDNA3luciferase (sample NIK), pcS3MTNIK, pcDNA3cγc and pcDNA3luciferase (sample NIK+cgc), pcS3MTNIK, a plasmid expressing GST (pGST) and pcDNA3luciferase (sample NIK+GST), pcS3MTNIK, pcDNA3cγc, pcGST and pcDNA3luciferase (sample NIK+GST+cgc), pcS3MTNIK, pcDNA3cγc, pcGST-41MDD and pcDNA3luciferase (sample NIK+cgc+41GST). The plasmids pcS3MTNIK, pcDNA3cγc, pcGST-41MDD and pcDNA3luciferase were used at concentrations of 0.5, 0.05, 2 and 0.5 μg/ml respectively.

Figure 8:
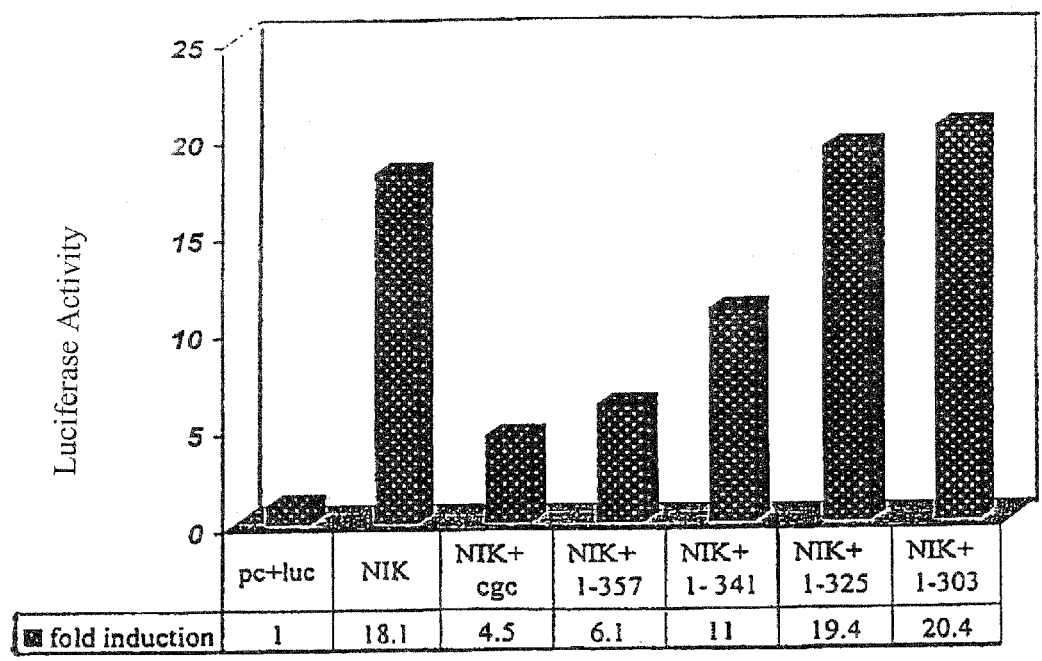

FIG. 8 shows the effect of cγc deletion mutants, deleted at the C-terminal end of the protein, and on NIK induced NF-κB activation. Activation of NF-κB is monitored by the luciferase reporter assay (for details see Example 10). NF-κB activation in Hela cells was induced by overexpressing NIK. Luciferase expression was monitored in cells transfected with the following plasmids: empty plasmid and a plasmid encoding luciferase under the control of an NF-κB inducible promoter (pcDNA3luciferase) (sample pc+luc), pcS3MTNIK and pcDNA3luciferase (sample NIK), pcS3MTNIK, pcDNA3cγc and pcDNA3luciferase (sample NIK+cgc), pcS3MTNIK, pcDNA3cγc3S7 and pcDNA3luciferase (sample NIK+1-357), pcS3MTNIK, pcDNA3cγc341 and pcDNA3luciferase (sample NIK+1-341), pcS3MTNIK, pcDNA3cγc325 and pcDNA3luciferase (sample NIK+1-325) and pcS3MTNIK, pcDNA3cγc303 and pcDNA3luciferase (sample NIK+1-303). Plasmids pcS3MTNIK, pcDNA3cγc/deleted, pcDNA3luciferase, were all used at the same concentration of 0.5 μg/ml. Total amount of DNA used was normalized with empty plasmid pcDNA3.

Figure 9:
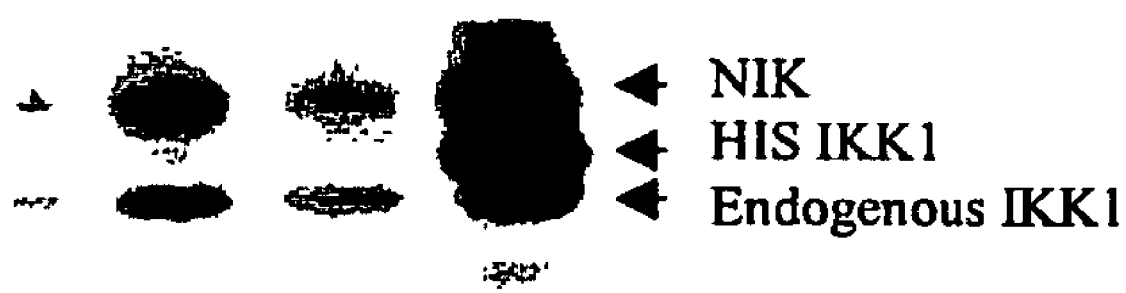

FIG. 9 shows the effect of cγc on the in vitro kinase activity of NIK. 293-T cells were transfected with 10 μg pcDNA3cγc (Line 1), 10 μg pcDNA3cγc and 10 μg of pcS3MTNIK (Line 2), 10 μg of pcS3MTNIK (Line 3) or 10 μg of pcS3MTNIK and 10 μg of a plasmid encoding the kinase IKK1 (pIKK1) (Line 4). 24 hours later, cells were harvested, lysed and immunoprecipitation was carried out with rabbit anti NIK antibody pre adsorbed to protein A sepharose beads. Kinase reaction was performed with 5 μci ATPγ as previously described (Uhlik et al. 1998).

Figure 10:
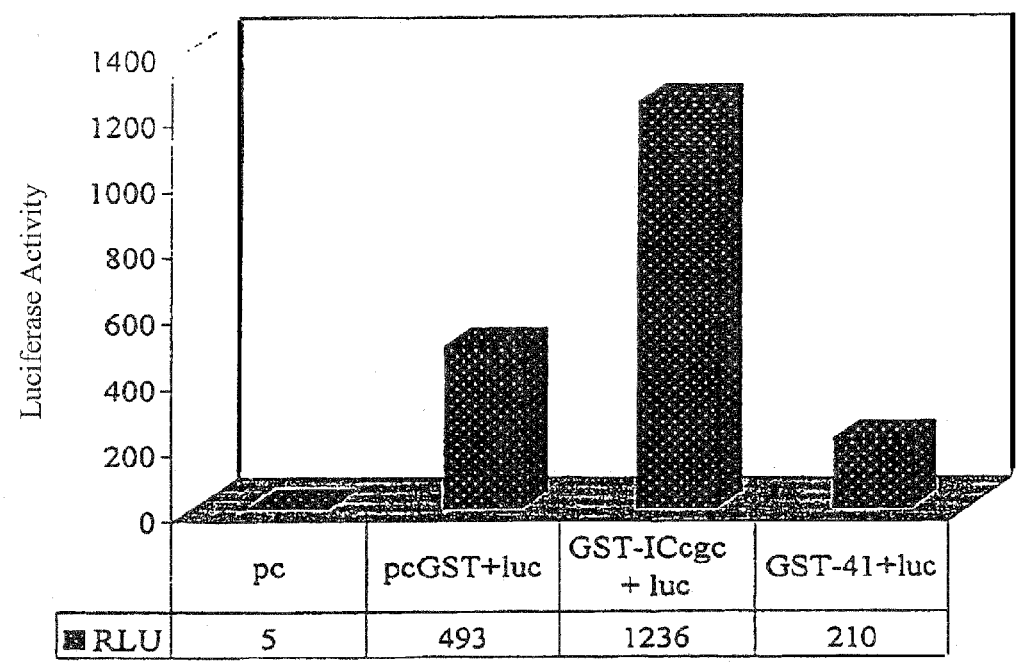

FIG. 10 shows the effect of overexpression of full ICD cγc or its 41 amino acid membrane distal domain on NF-κB activation induced via the LTβ receptor. Activation of NF-κB is monitored by the luciferase reporter assay (for details see Example 10). NF-κB activation in mouse embryonic fibroblast cells was induced with LTβ. Luciferase expression was monitored in cells transfected with the following plasmids: empty plasmid (sample pc), a plasmid expressing GST (pcGST) and pcDNA3luciferase (sample pcGST+luc), a plasmid encoding the GST fusion protein with the intracellular domain of cγc (pGSTICcγc) and pcDNA3luciferase (sample GSTICcgc+luc) and a plasmid encoding the GST fusion with the 41 polypeptide from the membrane distal domain of cγc (pGST41MDD) and pcDNA3luciferase (sample GST-41MDD+luc). Plasmids pGSTICcγc, pGST41MDD, and were used at 1 μg/well and pcDNA3luciferase were used at a concentration of 0.5 μg/well. Empty plasmid, pcDNA3 was used as a carrier to normalize the total DNA concentration to 2 μg/well. The levels of luciferase activity are expressed in relative light units (RLU).

FIG. 11 shows the amino acid sequence of the intracellular domain of cγc (SEQ ID NO:1).

FIG. 12 shows the amino acid sequence of the 41 amino acid polypeptide from the membrane distal domain of cγc (41MDD) (SEQ ID NO:2).

FIG. 13 shows the nucleotide sequence of the intracellular domain of cγc (cγcICD) (SEQ ID NO:5).

FIG. 14 shows the nucleotide sequence of the 41 polypeptide from the membrane distal domain of cγc (41MDD) (SEQ ID NO:6).

FIG. 15 shows the sequence of 12 aminoacids at the C-terminus of cγc involved in binding NIK (SEQ ID NO:3).

FIG. 16A shows interaction of endogenous NIK and cγc. Peripheral blood mononuclear cells (PMBC) (500×10$^6$ cells) were incubated either in the presence of IL-2 or IL-15, lysed and immunoprecipitated (IP) with anti cγc antibodies (for immunoprecipitation see Example 9). Co-immunoprecipitated proteins bound to cγc were detected in Western blots (WB) using relevant antibodies. The antibodies used in WB to detect co-immunoprecipitation with cγc were ANTI-NIK, ANTI-IKKα (IKK-1), ANTI-IKKβ (IKK2), and ANTI-IKKγ (NEMO). The co-immunoprecipitated proteins were in lysates of cells tested at 0 and up to four-hour incubation with IL-2 and 0 and up to one-hour with IL-15. A non-relevant IgG was used for immunoprecipitation (IP) as the control.

FIG. 16B shows that the signalosome co-immunoprecipitated with cγc is active. The immunoprecipitates prepared as in FIG. 16A were tested in a kinase assay (see details on Example 11) using GST-IKBα1-54 as a substrate for phosphorylation.

DETAILED DESCRIPTION OF THE INVENTION

The invention relates to the modulation of common gamma chain (cγc) and NIK interaction in pathologies involving said interaction.

The invention is based on the finding that cγc and NIK interact, and that this interaction has an effect on the activity of NIK.

Cγc and NIK interaction was detected using a C-terminal fragment of NIK (624-947) as bait in a two-hybrid screen of a bone marrow cDNA library. This interaction was confirmed by co-immunoprecipitation studies carried out in lysates of mammalian cells overexpressing NIK and cγc and also by co-immunoprecipitation studies in cells naturally expressing NIK and cγc. Immunoprecipitation studies revealed that cγc is efficiently co-precipitated with either the C-terminus of NIK (from residue 624 to 947, SEQ ID NO:19) or with the full length of NIK.

Cγc and NIK interaction was shown to occur not only in transfected mammalian cells overexpressing NIK and cγc, but also in non-transfected mononuclear peripheral blood cells with endogenous NIK and cγc.

Multiple deletion mutants of both cγc and NIK were generated to define the binding domains in both proteins. The interactions were tested by yeast 2 hybrid tests and/or by immunoprecipitation studies (see examples below). Domains of cγc responsible for binding NIK were found in the membrane proximal domain (MPD) of cγc comprising 44 amino acid residues (from residue 282 to 325), named 44MPD (see SEQ ID NO: 17) and, in a membrane distal domain (MDD) comprising 41 amino acid (from residues 329 to 369), named 41MDD (see SEQ ID NO: 2 and FIG. 12). When 12 amino acids at the end of cγc (cγc residues 358-369, FIG. 15 SEQ ID: NO 3 nucleotide sequence in SEQ ID NO: 4) were deleted from the intracellular domain of cγc (cγcICD), the binding to NIK decreases by 50% indicating that these residues play a major role in binding.

In addition, mutagenesis was carried out in residues located within the 41MDD, to define the specific amino acids interacting with NIK. The interaction of proline rich motifs in signaling proteins with their cognate domains is well documented (Kay B K, Williamson M P, Sudol M. FASEB J 2000 Feb. 14 (2): 231-421). 20% of the amino acids in the membrane distal 41 amino acids of cγc are prolines. Therefore, two consecutive prolines were mutated to alanine at two different sites within the 41 membrane distal amino acids of cγc: 1—PP 336,337AA and 2—PP360, 361AA and the effect of the mutation on binding of NIK tested by the two hybrid assay. The results obtained of cγc mutagenesis demonstrate that the prolines at residues 360 and 361 are important for the binding to NIK. Thus the muteins of the present invention retains prolines at residues 360 and 361.

A domain of NIK, responsible for cγc binding, comprises 81 amino acid residues from the C-terminus of NIK (from residue 624 to 947), named NIK640-720 (see SEQ ID NO: 18).

Cγc and NIK interaction was shown to be functionally significant. Reporter gene assays showed that cγc modulates NIK-induced NF-κB activation. It is possible, under experimental conditions, to induce NF-κB activation by overexpressing NIK. Activation of NF-κB can be monitored in cells transfected with a construct encoding luciferase under the control of an NF-κB inducible promoter. Using this luciferase system, NF-κB activation was monitored in cells overexpressing NIK alone or together with different concentration of cγc (for details see examples below). It was found that modulation of NF-κB depends on the concentration of NIK vis a vis the concentration of cγc within the cells (NIK/cγc). For example, enhancement of NIK mediated NF-κB activation was observed when NIK/cγc was above 1 while inhibition of NIK mediated NF-κB activation was observed when NIK/cγc was about equal or below 1.

Studies carried out with a dominant negative mutant of NIK showed that the NF-κB enhancing activity of cγc is specifically exerted via NIK.

One of the cγc fragments comprising the NIK binding domain, 41MDD, was tested for interference with cγc-NIK interaction and therefore for modulating NIK mediated NF-κB activation in the luciferase system. For this purpose luciferase expression (or NF-κB activation) was measured in transfected cells overexpressing NIK and cγc at a ratio above 1. Under these conditions cγc enhances the activation of NF-κB induced by NIK. The effect of 41MDD, containing the NIK binding region, was monitored in cells overexpressing NIK and cγc. It was found that overexpressing 41MDD could inhibit NIK mediated NF-κB activation, probably by inhibiting cγc-NIK interaction.

Alternatively, overexpressing the C-terminus of NIK (residues 624-947), comprising the cγc binding domain, together with cγc and NIK showed similar effect as 41MDD.

NIK's activation appears to have strict structural-requirements. A mutant of NIK, AlyNIK (glycine to arginine at codon 860 in human and codon 855 in mouse) was found to bind to cγc but was unable to increase NIK mediated NF-κB activation. Thus, even though both aly-NIK and wild type NIK showed binding to cγc and similar levels of NF-κB activation upon overexpression, cγc co-expression did not enhance NF-κB activation by aly-NIK.

These results indicate that AlyNIK or fragments thereof can be used to regulate NIK-cγc interaction.

Progressively C-terminus deleted cγc, 1-357, 1-341, 1-325, 1-303, were tested for their ability to modulate NF-κB mediated by NIK in the luciferase system. For this purpose luciferase expression and activation of NF-κB was measured in transfected cells overexpressing NIK and cγc or cγc deleted mutants at a ratio of about 1. Under these conditions cγc inhibits NF-κB activation induced by NIK. It was found that full length cγc and fragments 1-357 and 1-341 were able to inhibit NIK mediated NF-κB activation while mutants lacking the NIK binding domain such as fragments 1-325 and 1-303 did not have any effect on the activity of NIK mediated NF-κB activation. The lack of effect of 1-325 and 1-303 confirms the involvement of the membrane distal domain of cγc-NIK interaction and the role of this interaction in NF-κB modulation.

As mentioned above, the interaction of NIK and cγc leads to modulation of NF-κB activity. A possible mechanism underlying modulation of NIK activity by cγc may be enhanced phosphorylation of NIK upon cγc/NIK interaction. In vitro kinase assay showed a three-fold enhancement by cγc of NIK self- and IKK1-phosphorylation. Thus, the result obtained in the in vitro kinase assay supports the hypothesis that modulation of NIK activity by cγc may be enhanced phosphorylation of NIK upon cγc/NIK interaction.

Induction of the lymphotoxin beta (LTβ) receptor by its ligand results in NF-κB activation. It is suggested in the literature that NIK is activated by inducing the LTβ receptor with its ligand. The effect of overexpressing the intracellular domain of cγc polypeptide (cγcICD) or its 41 membrane distal domain (41MDD) was tested when NF-κB is activated by triggering the LTβ receptor and this activation is believed to be mediated by endogenous NIK. ICDcγc expression enhanced the NF-κB activation by LTβ by 2.5 fold, while 41MDD expression inhibited by 50% NF-κB activation by LTβ. These results suggest that lymphotoxin stimulation and NF-κB modulation involves cγc-NIK interaction. These results suggest that lymphotoxin stimulation and NF-κB modulation involves cγc-NIK interaction. These results show that the cγcICD polypeptide or the 41 MDD can modulate signaling triggered through the LTβ receptor and demonstrate, once more, that ICDcγc polypeptide or fragments thereof may serve as candidates for peptide based drug designing. Such drugs may modulate NIK action and therefore are valuable in preventing or alleviating diseases in which the action of NIK is involved in their pathogenesis. NIK has been shown to induce NF-κB activation, thus cγc fragments of the invention may be used to treat and/or prevent diseases in which NF-κB is involved in their pathogenesis.

The results obtained revealed that signalling through cγc involves NIK and recruitment of signalosome proteins and consequently modulation of NF-κB. Therefore fragments of NIK, for example those comprising the C-terminus (from residue 624 to 947) and NIK640-720 the cγc-binding domain could be used to modulate signalling through cγc.

As mentioned above, interaction of endogenous NIK and cγc was demonstrated in peripheral mononuclear blood cells. It was found that in mononuclear cells NIK is constitutively associated with cγc, and upon IL-2 induction the signalosome components IKK-1, IKK-2, and IKK-3 are recruited to the IL-2 receptor through cγc. The IL-2 receptor common γ chain was found to bind to NIK at a different location, other than IKK-1 binding region. Similar results were obtained upon stimulation of the cells with IL-15.

The signalosome components co-immunoprecipitated with cγc upon IL-2 stimulation was shown to be active in a kinase assay. Thus these results demonstrate that under physiological conditions, binding of endogenous cγc to NIK occurs, and that this interaction is involved in NIK activity and in NIK dependent NF-κB activation. Therefore inhibiting the interaction of cγc and NIK may bring about inhibition of NF-κB activation.

The results obtained demonstrate that the interaction of NIK and the signalosome components with cγc is required for signalling of IL-2. Therefore, inhibition of the cγc and NIK interaction may inhibit IL-2 signal. Thus, cγc binding domain in NIK, NIK640-720 or a mutein, fusion protein, functional derivative, circularly permutated derivative or fragment thereof can be used to inhibit IL-2 signaling. Similar results were obtained by stimulating mononuclear peripheral blood cells with IL-15. Thus the polypeptides of the invention can be used to treat any disease in which activation of a cytokine, having the common gamma chain in their receptors is involved in pathogenesis or any diseases in which a cytokine stimulating signalling trough cγc is involved in the pathogenesis of a disease.

Alternatively, these polypeptides of the invention may be used to enhance the activity of cytokines to treat any disease in which activation of a cytokine, having the common gamma chain in their receptors can cure or alleviate a disease.

Examples of cytokines using cγc for signal transduction are IL-2, IL-4, IL-7, IL-9, IL-13, IL-15 and IL-21.

The invention relates to the use of NIK and to fragments thereof and to their salts, functional derivatives, precursors and active fractions as well as its active mutants, i.e. other proteins or polypeptides wherein one or more amino acids of the structure are eliminated or substituted by other amino acids or one or more amino acids were added to that sequence in order to obtain polypeptides or proteins having the same activity such as modulation of cγc-NIK interaction and/or NF-κB activation and/or cγc signalling and comprises also the corresponding "fusion proteins" i.e. polypeptides comprising said polypeptides or a mutation thereof fused with another protein Said polypeptides can therefore be fused with another protein such as, for example, an immunoglobulin.

The term "salts" herein refers to both salts of carboxyl groups and to acid addition salts of amino groups of said polypeptides of the invention or muteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulphuric acid, and salts with organic acids such as, for example, acetic acid or oxalic acid. Of course, any such salts must have substantially similar activity to said polypeptides of the invention or its muteins for example allow modulation of cγc-NIK interaction and/or NF-κB activation and/or cγc signalling.

The definition "functional derivatives" as herein used refers to derivatives which can be prepared from the functional groups present on the lateral chains of the amino acid moieties or on the terminal N- or C-groups according to known methods and are comprised in the invention when they are pharmaceutically acceptable i.e. when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alkanoyl- or aroyl-groups.

"Fragment" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of said polypeptides of the invention for example, allow modulation of cγc-NIK interaction and/or NF-κB activation and/or cγc signalling.

The term "circularly permutated" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permutated molecule may be synthesized de novo as a linear molecule and never go through a circularization and opening step. The particular circular permutation of a molecule is designated by brackets containing the amino acid residues between which the peptide bond is eliminated. Circularly permutated molecules, which may include DNA, RNA and protein, are single-chain molecules, which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

The terms said "polypeptide and/or protein" of the invention are interchangeable and refer to NIK and fragments of NIK comprising regions responsible for binding cγc such as the C-terminus domain and NIK640-720 and the AlyNIK.

The present invention also concerns muteins of polypeptides of the invention, which muteins retain essentially the same biological activity of said protein of the invention for example, allow modulation of cγc-NIK interaction and/or NF-κB activation and/or cγc signalling, having essentially only the naturally occurring sequences of said proteins of the invention. Such "muteins" may be ones in which up to about 25% and preferably under 12% amino acid residues may be deleted, added or substituted by others in the polypeptide, such that modifications of this kind do not substantially change the biological activity of the protein mutein with respect to the protein itself for example, allow modulation of cγc-NIK interaction and/or NF-κB activation and/or cγc signalling.

These muteins are prepared by known synthesis and/or by site-directed mutagenesis techniques, or any other known technique suitable thereof.

Any such mutein preferably has a sequence of amino acids sufficiently duplicative of that of the basic NIK and fragments of NIK comprising regions responsible for binding cγc such as the C-terminus domain (from residue 624 to 947), NIK640-720 and the AlyNIK mutant such as to have substantially similar activity thereto. Thus, it can be determined whether any given mutein has substantially the same activity as the basic protein of the invention by means of routine experimentation comprising subjecting such a mutein to the biological activity tests set forth in Examples below.

Muteins of the protein which can be used in accordance with the present invention, or nucleic acid coding thereof, include a finite set of NIK and fragments of NIK comprising regions responsible for binding cγc such as the C-terminus domain and NIK640-720 and the AlyNIK corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978; and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see. See Ausubel et al., Current Protocols in Molecular Biology, Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

Preferred changes for muteins in accordance with the present invention are what are known as "conservative" substitutions. Conservative amino acid substitutions of those in the protein having essentially the naturally-occurring said protein of the invention sequences, may include synonymous amino acids within a group, which have sufficiently similar physicochemical properties that substitution between members of the group will preserve the biological function of the molecule, see Grantham, Science, Vol. 185, pp. 862-864 (1974). It is clear that insertions and deletions of amino acids may also be made in the above-defined sequence without altering its function, particularly if the insertions or deletions only involve a few amino acids, e.g., under 25%, and preferably under 12% and do not remove or displace amino acids which are critical to a functional conformation, e.g., cysteine residues, Anfinsen, "Principles That Govern The Folding of Protein Chains", Science, Vol. 181, pp. 223-230 (1973). Muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE C

Most Preferred Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Examples of production of amino acid substitutions in proteins which can be used for obtaining muteins of the protein for use in the present invention include any known method steps, such as presented in U.S. Pat. RE 33,653, U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Straw et al).

In another preferred embodiment of the present invention, any mutein of said protein for use in the present invention has an amino acid sequence essentially corresponding to that of the above noted protein of the invention for example: NIK and fragments of NIK comprising regions responsible for binding cγc such as the C-terminus domain and NIK 640-720 and the AlyNIK protein or fragments thereof. The term "essentially corresponding to" is intended to comprehend muteins with minor changes to the sequence of the basic protein which do not affect the basic characteristics thereof, particularly insofar as its ability to the said protein of the invention is concerned. The type of changes which are generally considered to fall within the "essentially corresponding to" language are those which would result from conventional mutagenesis techniques of the DNA encoding the said protein of the invention, resulting in a few minor modifications, and screening for the desired activity for example, allow modulation of cγc-NIK interaction and/or NF-κB activation and/or cγc signalling.

The present invention also encompasses variants of said proteins of the invention. Preferred variants are the ones having at least 80% amino acid identity, a more preferred variant is one having at least 90% identity and a most preferred variant is one having at least 95% identity to said proteins of the invention.

The term "sequence identity" as used herein means that the amino acid sequences are compared by alignment according to Hanks and Quinn (1991) with a refinement of low homology regions using the Clustal-X program, which is the Windows interface for the ClustalW multiple sequence alignment program (Thompson et al., 1994). The Clustal-X program is available over the internet at ftp://ftp-igbmc.u-strasbg.fr/pub/clustalx/. Of course, it should be understood that if this link becomes inactive, those of ordinary skill in the art could find versions of this program at other links using standard internet search techniques without undue experimentation. Unless otherwise specified, the most recent version of any program referred herein, as of the effective filing date of the present application, is the one, which is used in order to practice the present invention.

Another method for determining "sequence identity" is he following. The sequences are aligned using Version 9 of the Genetic Computing Group's GDAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Muteins in accordance with the present invention include those encoded by a nucleic acid, such as DNA or RNA, which hybridizes to DNA or RNA under stringent conditions and which encodes said protein in accordance with the present invention, comprising essentially all of the naturally-occurring sequences encoding for example NIK and fragments of NIK comprising regions responsible for binding cγc such as the C-terminus domain and NIK640-720 and the AlyNIK mutant.

The term "hybridization" as used herein shall include any process by which a strand of nucleic acid joins with complementary strand through a base pairing (Coombs J, 1994, Dictionary of Biotechnology, Stockton Press, New York N.Y.). "Amplification" is defined as the production of additional copies of a nucleic acid sequence and is generally carried out using polymerase chain reaction technologies well known in the art (Dieffenbach and Dveksler, 1995, PCR Primer, a Laboratory Manual, Cold Spring Harbor Press, Plainview N.Y.).

"Stringency" typically occurs in a range from about Tm−5° C. (5° C. below the melting temperature of the probe) to about 20° C. to 25° C. below Tm.

The term "stringent conditions" refers to hybridization and subsequent washing conditions, which those of ordinary skill in the art conventionally refer to as "stringent". See Ausubel et al., Current Protocols in Molecular Biology, Greene Publications and Wiley Interscience, New York, N.Y., 1987-1995;

Sambrook et al., Molecular Cloning: A Laboratory Manual, Cold Spring Harbor Laboratory, Cold Spring Harbor, N.Y., 1989.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm=81.5C.+16.6\ (\mathrm{Log}M)+0.41\ (\%\ GC)-0.61\ (\%\ \mathrm{form})-500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to the equation of Meinkoth, hybridization will occur even if there is up to about 10% mismatch.

As used herein, "highly stringent conditions" are those which provide a Tm which is not more than 10° C. below the Tm that would exist for a perfect duplex with the target sequence, either as calculated by the above formula or as actually measured. "Moderately stringent conditions" are those that provide a Tm, which is not more than 20° C. below the Tm that would exist for a perfect duplex with the target sequence, either as calculated by the above formula or as actually measured. Without limitation, examples of highly stringent (5-10° C. below the calculated or measured Tm of the hybrid) and moderately stringent (15-20° C. below the calculated or measured Tm of the hybrid) conditions use a wash solution of 2×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those that allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE (standard saline-phosphate-EDTA), 5×Denhardt's reagent, 0.5% SDS, 100μg/ml denatured, fragmented salmon sperm DNA at a temperature approximately 20 to 25° C. below the Tm. If mixed probes are used, it is preferable to use tetramethyl ammonium chloride (TMAC) instead of SSC (Ausubel, 1987, 1999).

A fragment of NIK640-720 may serve as a candidate for peptide based drug designing. Organic molecules, based on the structure of these binding fragments, which may interfere in binding of cγc to NIK, can be designed. Such organic molecules can be used as drugs that can modulate NIK action and will be of value in preventing inflammatory responses and other disorders in which NIK and cγc interaction is involved in their pathogenesis.

"Intrabodies" are specific antibodies that are transduced in a cell and are capable of inhibiting an undesired associated reaction such as NIK and cγc interaction, wherein said antibody when expressed will bind in the cell to a target molecules and/or ligand involved in the undesired associated reaction, expressing the antibody and letting said antibody bind to said target receptor and/or ligand. The use of intrabodies is disclosed in WO9914353.

Antibodies can be prepared against NIK 640-720 and transduced in cells for inhibiting NIK and cγc interactions in a disease in which the activity of NIK is involved in its pathogenesis.

Activation of NF-κB involves migration into the nucleus of the cell and activation of a large number of proinflammatory genes.

In disorders such as rheumatoid arthritis (in the case of inflammation), osteoarthritis, asthma, cardiac infarct, Alzheimer's disease, or atherosclerosis, NF-κB is activated beyond the normal extent. The inhibition of NF-κB is also of benefit in cancer therapy, since it is employed there for the reinforcement of the cytostatic therapy.

The polypeptides of the invention may be produced, in eukaryotic or eukaryotic expression systems, intracellulary, periplasmic or may be secreted into the medium. The produced NIK such as 41MDD and 44MPD, 1-357 and 1-341 and/or NIK and fragments of NIK comprising regions responsible for binding cγc such as the C-terminus domain (from residue 624 to 947), NIK640-720 and the AlyNIK mutant, may be recovered in soluble or insoluble form (inclusion bodies).

A vector comprising DNA encoding said polypeptides of the invention might be used for expression of said polypeptides in prokaryotic or eukaryotic systems.

An expression vector encoding an effective signal peptide, such as the human growth hormone signal peptide, fused to the DNA encoding of e.g. NIK and fragments of NIK comprising regions responsible for binding cγc such as the C-terminus domain (from residue 624 to 947), NIK640-720 and the AlyNIK mutant may be used for eukaryotic expression and secretion.

The present invention provides NIK and fragments of NIK comprising regions responsible for binding cγc such as the C-terminus domain (from residue 624 to 947), NIK640-720 and the AlyNIK mutant, peptides derived therefrom, or a mutein, fusion protein, functional derivative, circularly permutated derivative or fragment thereof, or salt thereof for the manufacture of a medicament for the treatment of inflammatory diseases.

A therapeutic or research-associated use of these tools necessitates their introduction into cells of a living organism. For this purpose, it is desired to improve membrane permeability of peptides, proteins and oligonucleotides. Derivatization with lipophilic structures may be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al., 1991. Further modifications of peptides and proteins comprise the oxidation of methionine residues to thereby create sulfoxide groups, as described by Zacharia et al. 1991. Zacharia and co-workers also describe peptide or derivatives wherein the relatively hydrophobic peptide bond is replaced by its ketomethylene isoester (COCH2). These and other modifications known to the person of skill in the art of protein and peptide chemistry enhance membrane permeability.

Another way of enhancing membrane permeability is the use receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al. 1998, and references therein. The CD4, GPR1, GPR15, and STRL33 molecules have been identified as receptors/co-receptors for HIV, see Edinger et al. 1998 and references therein.

Thus, conjugating peptides, proteins or oligonucleotides to molecules that are known to bind to cell surface receptors will enhance membrane permeability of said peptides, proteins or oligonucleotides. Examples of suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, proteins and oligonucleotides, and the preparation of said conjugates.

Low and co-workers further teach that molecules such as folate or biotin may be used to target the conjugate to a multitude of cells in an organism, because of the abundant and unspecific expression of the receptors for these molecules.

The above use of cell surface proteins for enhancing membrane permeability of a peptide, protein or oligonucleotide of the invention may also be used in targeting said peptide, protein or oligonucleotide of the invention to certain cell types or tissues. For instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al., 1998, teaches the use of folate to target cancer cells, and Zhang et al. 1998, teaches the relative abundance of each of the other antigens noted above in various types of cancer and in normal cells.

The protein, peptide or oligonucleotide of the invention may therefore, using the above-described conjugation techniques, be targeted to certain cell type as desired. For instance, if it is desired to inhibit activation of NIK in cells of the lymphocytic lineage, NIK and fragments of NIK comprising regions responsible for binding cγc such as the C-terminus domain (from residue 624 to 947), NIK640-720 and the AlyNIK, fragment thereof, mutants and derivatives of the invention may be targeted at such cells, for instance, by using the MHC class II molecules that are expressed on these cells. This may be achieved by coupling an antibody, or the antigen-binding site thereof, directed against the constant region of said MHC class II molecule to the protein or peptide of the invention. Further, numerous cell surface receptors for various cytokines and other cell communication molecules have been described, and many of these molecules are expressed with in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule.

The proteins, peptides and antisense sequences of the invention may be introduced into cells by the use of a viral vector. The use of vaccinia vector for this purpose is detailed in chapter 16 of Current Protocols in Molecular Biology. The use of adenovirus vectors has been described e.g. by Teoh et al., 1998, Narumi et al, 1998, Pederson et al, 1998, Guang-Lin et al., 1998, and references therein, Nishida et al., 1998, Schwarzenberger et al 1998, and Cao et al., 1998. Retroviral transfer of antisense sequences has been described by Daniel et al. 1998.

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., 1998 teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes, which may be used to target, said viral vector. For instance, cytokine epitopes, MHC class II-binding peptides, or epitopes derived from homing molecules may be used to target the viral vector in accordance with the teaching of the invention.

The present invention encompasses pharmaceutical compositions comprising one or more active substance selected from one or more NIK and fragments of NIK comprising regions responsible for binding cγc such as the C-terminus domain (from residue 624 to 947), NIK640-720 and the AlyNIK and/or DNA or vectors harbouring their sequences or antisense.

The present invention encompasses pharmaceutical compositions comprising specific antibodies able to recognise and bind NIK and fragments of NIK comprising regions responsible for binding cγc.

The term "antibody" is meant to include polyclonal antibodies, monoclonal antibodies (MAbs), chimeric antibodies, anti-idiotypic (anti-Id) antibodies to antibodies that can be labelled in soluble or bound form, and humanized antibodies as well as fragments thereof provided by any known technique, such as, but not limited to enzymatic cleavage, peptide synthesis or recombinant techniques.

A monoclonal antibody contains a substantially homogeneous population of antibodies specific to antigens, which populations contain substantially similar epitope binding sites. Mabs may be obtained by methods known to those skilled in the art. See, for example Kohler and Milstein, Nature, 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of Mabs in vivo or in situ makes this the presently preferred method of production.

Chimeric antibodies are molecules of which different portions are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al., *Proc. Natl. Acad. Sci. USA* 81:3273-3277 (1984); Morrison et al.,

*Proc. Nat. Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066-1074 (1986); Robinson et al., International Patent Application No. WO8702671 (published May 7, 1987); Liu et al., *Proc. Natl. Acad. Sci USA* 84:3439-3443 (1987); Sun et al., *Proc. Natl. Acad. Sci USA* 84:214-218 (1987); Better et al., *Science* 240:1041-1043 (1988); Riechmann et al., *Nature* 332:323-327. and Harlow and Lane, ANTIBODIES: A LABORATORY MANUAL, supra. These references are entirely incorporated herein by reference.

"Fully humanized antibodies" are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully humanized antibodies and methods for their production are known in the art (Mendez et al., Nature Genetics 15:146-156 (1997); Buggemann et al., Eur. J. Immunol. 21:1323-1326 (1991); Tomizuka et al., Proc. Natl. Acad. Sci. USA 97:722-727 (2000) Patent WO 98/24893.

An anti-idiotypic (anti-Id) antibody is an antibody, which recognizes unique determinants generally associated with the antigen-binding site of an antibody. An Id antibody can be prepared by immunizing an animal of the same species and genetic type (e.g. mouse strain) as the source of the Mab to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original Mab, which induced the anti-Id. Thus, by using antibodies to the idiotypic determinants of a Mab, it is possible to identify other clones expressing antibodies of identical specificity.

Accordingly, Mabs generated against NIK, its isoforms, analogs, fragments or derivatives of the present invention may be used to induce anti-Id antibodies in suitable animals, such as BALB/c mice. Spleen cells from such immunized mice are used to produce anti-Id hybridomas secreting anti-Id Mabs. Further, the anti-Id Mabs can be coupled to a carrier such as keyhole limpet hemocyanin (KLH) and used to immunize additional BALB/c mice. Sera from these mice will contain anti-anti-Id antibodies that have the binding properties of the original Mab specific for an epitope of the above NIK protein, or analogs, fragments and derivatives thereof.

The anti-Id Mabs thus have their own idiotypic epitopes, or "idiotopes" structurally similar to the epitope being evaluated.

The term "monoclonal antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-325 (1983)).

A monoclonal antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three-dimensional structural characteristics as well as specific charge characteristics.

An "antigen" is a molecule or a portion of a molecule capable of being bound by an antibody, which antigen is additionally capable of inducing an animal to produce antibody capable of binding to an epitope of that antigen. An antigen may have one or more than one epitope. The specific reaction referred to above is meant to indicate that the antigen will react, in a highly selective manner, with an epitope on its corresponding antibody and not with the multitude of other antibodies, which may be evoked by other antigens.

The definition of "pharmaceutically acceptable" is meant to encompass any carrier that does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

The invention relates to the use of specific antibodies able to recognise and to NIK and/or fragments of NIK comprising regions responsible for binding cγc, in the manufacture of a medicament for the treatment of a disease, wherein a cytokine stimulating signalling trough IL-2 cγc is involved in the pathogenesis of the disease.

The invention relates to a method for the treatment of a disease involving signalling of a cytokine through cγc in the pathogenesis of said disease comprising administration of a therapeutically effective amount of specific antibodies able to recognise and bind cγc protein and/or to fragments of cγc comprising regions responsible for binding NIK such as 41MDD and 44MPD, 1-357 and 1-341, to a subject in need.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The present invention relates to a method of enhancing or inhibiting NIK response in a patient in need, e.g. a patient suffering from inflammatory disease and/or cancer, comprising administration of a therapeutically effective amount of NIK and fragments of NIK comprising regions responsible for binding cγc such as the C-terminus domain (from residue 624 to 947), NIK640-720 and the AlyNIK, a mutein, fusion protein, functional derivative, circularly permutated derivative or fragment thereof.

A "therapeutically effective amount" is such that when administered, the said polypeptides of the invention result in modulation of the biological activity of NIK, NF-κB and/or cγc signaling. The dosage administered, as single or multiple doses, to an individual may vary depending upon a variety of factors, including the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the activity of NIK cγc signaling and fragments thereof.

The NIK can be used in an assay to screen for potential therapeutically valuable molecules which modulates cγc-NIK interaction. Cells expressing NIK cγc and the reporter gene luciferase under an NF-κB inducible promoter are treated with individual small molecules. Luciferase expression (or NF-κB activation) is compared in treated cells vis a vis control cells. Candidate organic compounds able to modulate luciferase expression (i.e. NF-kb activity) are selected. The compounds tested may be obtained not only through combinatorial chemistry, but also by other high throughput synthesis methods. Automated techniques enable the rapid synthesis of libraries of molecules, large collections of discrete compounds, which can be screened. Producing larger and more diverse compound libraries increases the likelihood of discovering a useful drug within the library. For high throughput screening robots can be used to test inhibition of recruitment or disruption of signalosome formation by thousands of compounds.

In addition, screening for molecules generated by combinatorial chemistry that inhibit NIK and IL-2 receptor γ chain interaction comprising a polypeptide comprising the intracellular domain of the cγc or a mutein, fusion protein, functional derivative, active fraction, circularly permutated derivative or fragment thereof, comprising: coating or capturing (by a specific antibody bound to the plate) one of the proteins (e.g. NIK or NIK640-720) in a plate and detecting the binding of the other protein (e.g. cγc, ICDcγc or fragments thereof) bound to the plate with specific antibody in the presence or absence of organic compounds.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention will be now illustrated by the following non-limiting examples.

EXAMPLES

Example 1

Detection of Proteins Interacting with NIK by the Two-hybrid System Method:

The two-hybrid system method in yeast, widely used for detecting in-vivo protein-protein interaction, has been used to screen a DNA expression library to find and identify proteins that interact with NIK (see details in Example 8). A human bone marrow library has been selected based on evidence indicating a pivotal role of NIK in the lymphoid system development and function.

The N-terminal region of NIK contains a negative regulatory domain (NRD), which interacts with the C-terminal region of NIK, thereby inhibiting the binding of NIK to its substrates (IKK alpha and p100). Interaction between the C- and N terminal region of NIK prevents binding of NIK to its substrates. The C-terminus domain of NIK was found to be responsible for the binding of NIK to several key regulatory proteins such as TRAF-2, IKK-1 and to P100, suggesting that this domain may bind additional proteins, which are important for modulating its activities. Therefore, introducing the entire molecule, as bait in the two-hybridsystem is undesirable since the C-terminus domain may be occluded by the NRD. Thus, the C-terminus of NIK (amino acids 624-947) has been used as the bait in a two-hybrid screen (for details see Example 8).

More than 5000 clones appeared on the selection plates. About half of the resistant clones were analyzed by α-gal assay and approximately 60% of them turned out positive with varying intensity of blue colour. Plasmids were isolated and purified from 800 colonies. The DNA inserts of 400 plasmids out of the 800 (chosen according to colour intensity which is indicative of affinity of binding) were amplified by polymerase chain reaction (PCR) using primers corresponding to the flanking sequences of the inserts in the cDNA library, and sequenced. Most of the preys detected turned out to be non-specific, e.g.: 80% of the DNA inserts corresponded to 3' and 5' untranslated regions of various genes and 10% to DNA inserts encoding immunoglobulins. The remaining 10% corresponded to segments encoding regions of proteins. Some of the positive colonies turned blue 4-8 days after seeding, some after about 8-12 days, and others became coloured late, up to 12-16 days after seeding. The speed of the colour development in positive colonies is indicative of the strength of protein-protein interaction, i.e. the faster the colour appears, the stronger the interaction.

One of the binding proteins found, the IL-2 receptor gamma chain, was chosen for further analysis. The IL-2 receptor gamma chain is a subunit of the IL-2, IL-4, IL-7, IL-9, IL-13, IL-15 and IL-21 receptor complexes; therefore, it is commonly dubbed as the 'common γ chain' (cγc).

Example 2

Evaluation of IL-2 Gamma Chain-NIK Interactions in a Mammalian Environment:

The detection of a specific interaction between two different mammalian proteins in a two-hybrid system in yeast does not necessarily imply that there exists a corresponding interaction between the proteins in a native mammalian environment. Therefore, in order to verify NIK and cγc interaction in a mammalian environment, co-immunoprecipitation studies of NIK and cγc were carried out in lysates of 293-T cells overexpressing these proteins (for details see Example 9).

To overexpress NIK and cγc, 293-T cells were co-transfected with equal amounts of NIK and cγc expression plasmids (pcS3MTNIK, myc tag at its N-terminus and pcDNA3 cγc respectively, both plasmids having similar molecular weight). The overexpressed proteins were immunoprecipitated with antibodies specific for one of the proteins (e.g. NIK) and the presence of a coprecipitated protein (e.g. cγc) was detected by Western blots analysis.

Figure 2:
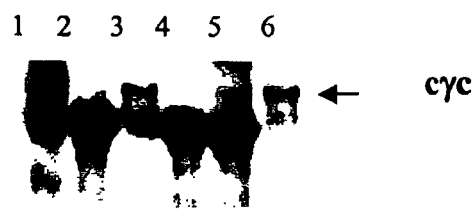
FIG. 2 shows results on NIK-cγc interaction in mammalian cells monitored by immunoprecipitation assay. Western blot analysis were detected with anti cγc antibody of the following samples: 1—lysates of 293-T cells transfected with pcDNA3cγc and immunoprecipitated with anti cγc, 2—lysates of 293-T cells transfected with pcDNA3cγc and immunoprecipitated with anti NIK antibody. 6—lysates of 293-T cells transfected with pcS3MTNIK (expressing myc tagged NIK) and pcDNA3cγc and NIK immunoprecipitated with anti myc antibody. 3—the same as in 6 only that the pcS3MTNIK is exchanged with the pcS3MTNIKaly. 4—lysates of 293-T cells transfected with pcdnNIK (C-terminal domain of NIK residues 624-947) and immunoprecipitated with anti cγc antibody and 5—lysates of 293-T cell transfected with pcdnNIK and pcDNA3cγc immunoprecipitated with anti NIK antibodies (not anti myc antibody as in 3 and 6).

FIG. 2 summarized the results of Western blot analysis of immunoprecipitates detected with anti cγc antibodies. The samples analysed were the following: 1—a lysate of cells overexpressing cγc and immunoprecipitated with anti cγc. This sample is the positive control for the immunoprecipitation method. A strong signal corresponding to the molecular weight of cγc was observed. 2—a lysate of cells overexpressing cγc alone and immunoprecipitated with anti NIK antibody. This sample in the experiment was performed to check co-immunoprecipitation of cγc with endogenous NIK protein, which is present at minor concentrations and probably in inactive form, and also to check the specificity of the anti NIK antibodies. A protein with a molecular weigh corresponding to cγc was not detected in the blot. 6—a lysate of cells overexpressing both myc tagged NIK and cγc and immunoprecipitated with anti myc antibody. Cyc is co immunoprecipitated together with NIK, demonstrating that cγc-NIK interaction occurs also in the native environment. 3—the same as 6 with the difference that NIK is exchanged for the NIK aly mutant (mutation in human is G860R corresponding to aly mutation in mouse G855R). Cγc is co-immunoprecipitated with NIK aly mutant indicating that the mutant is capable of binding cγc as efficient as the wild type NIK. 4—a lysate of cells overexpressing the C-terminus of NIK (amino acids 624-947), the same fragment of NIK employed as bait in the two-hybrid system. A band corresponding to cγc was not detected in the blot. 5—a lysate of cells overexpressing both the C-terminus of NIK and cγc and immunoprecipitation with anti NIK antibody. Cγc efficiently coprecipitated with the C-terminus of NIK.

These results show that cγc is efficiently co-precipitated with either the C-terminus of NIK (used as the bait in the two hybrid system in which the cγc was identified) or with the full length NIK.

Figure 3:
FIG. 3 shows results on NIK-cγc interaction in mammalian cells monitored by immunoprecipitation assay. Western blot analysis of immunoprecipitates and total 293-T cell lysates detected with anti NIK antibody. The samples analysed were the following.

FIG. 3 summarizes the results of Western blot analysis of immunoprecipitates and total cell lysates detected with anti NIK antibody. The samples analysed were the following: 3—a lysate of cells overexpressing NIK alone immunoprecipitated with anti NIK. This sample is the positive control for the immunoprecipitation method. A strong signal of the molecular weight corresponding to NIK was observed. 2—a lysate of cells overexpressing NIK alone and immunoprecipitated with anti cγc antibody. A protein with a molecular weigh corresponding to NIK could not be detected. This result demonstrates also the specificity of the cγc antibodies.

1—lysates of cells overexpressing both NIK and cγc immunoprecipitated with anti cγc antibody. The results show that NIK is effectively coimmunoprecipitated with cγc. 5—is a lysate of non-transfected cells, 4 and 6 are lysates of cells overexpressing both NIK and cγc or cells overexpressing NIK alone respectively before immunoprecipitation. A strong band corresponding to the molecular weight of NIK was observed in the blot, demonstrating that it is overexpressed.

The results obtained by Western blots analysis of immunoprecipitates showed bi-directional precipitation of NIK and cγc demonstrating that their interaction occurs also in mammalian cells. The C-terminus domain of NIK, the full length NIK and the mutant NIKaly (NIK-G860R) are all coimmunoprecipitable by cγc.

Example 3

Figure 1:
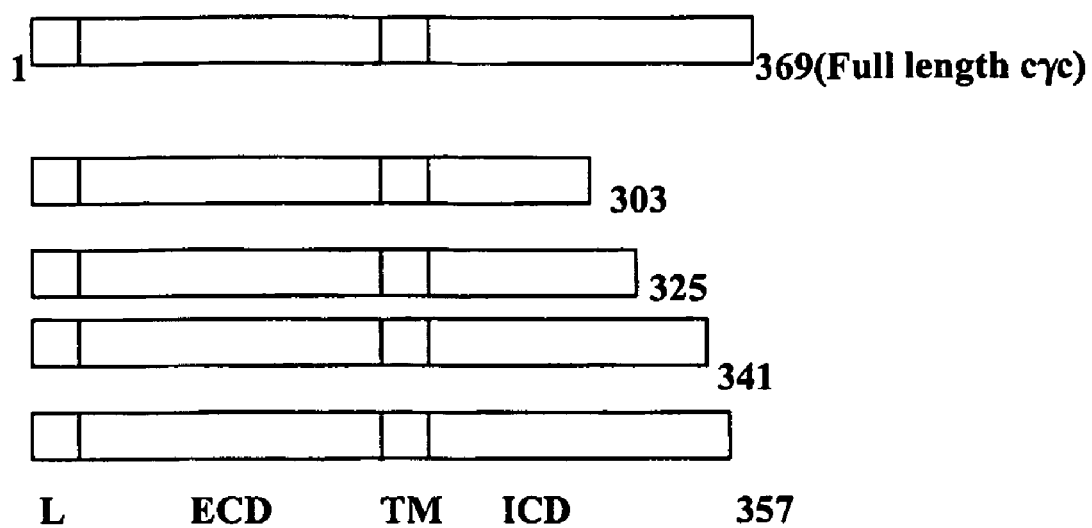
FIG. 1 shows a schematic representation of cγc domains and the residues in which stop codons were introduced to generate deletion mutants. L-Leader 1-23, ECD-extra cellular domain, TM-trans membrane domain, ICD-intra cellular domain.

Mapping the Region in cγc Responsible for Binding NIK:

To define the domain of cγc responsible for binding NIK, deletion mutants of cγc have been created and their binding to NIK analysed (FIG. 1).

The deletion mutants were created by sequentially introducing stop codons in the cytoplasmic domain of cγc, in gaps of 10-20 amino acids. The DNA encoding the full-length cγc or its deletion mutants were introduced into the pGADT7 prey vector (Clontech) for testing their binding to NIK in the SFY526 heterologous yeast strain by the two hybrid assay. The SFY526 yeast strain is prototrophic for TRP and Leu. pGBKT plasmids (bait vector) have the Trp1 wild type gene and pGAD has the wild type Leu2 gene. Thus, only doubly transfected yeast will grow on selective Leu Trp media. Functional GAL4 will be restored in doubly transfected yeast when the chimeric proteins fused to GAL4 domains interact, bringing the activation domain and DNA binding domain of GAL4 to close proximity. The level of LAC-Z expression is indicative of the strength of the protein-protein interaction. Lac-Z activity was assessed by the standard beta-gal/colony lift filter assay (Clontech, Yeast Protocol Handbook, Chapter VI).

Since introduction of cγc and mutants into the pGADT7 prey vector for assessing their binding to NIK as bait manifested high non-specificity, the interactions were tested in the reverse orientation: i.e. deletion mutants were cloned into the bait vector and NIK or C-terminus of NIK (residues 624-947) in the pray vector. The results summarized in Table D show that none of the deletions, but the cytoplasmic domain of cγc (ICD) alone showed strong binding, to both NIK and NIK C-terminus. The binding of most of the ICD (lacking 5 amino acid from its proximal membrane domain) to both NIK and C-terminus NIK was stronger than that of the full-length cγc molecule. A 50% reduction in affinity to NIK was observed by deleting 12 amino acids or 44 amino acids at the membrane distal end of cγcICD.

TABLE D

| cγc amino acid residues | NIK624-947 (C-terminal domain) | NIK | Lamin |
|---|---|---|---|
| Full length (1-369) | +/− | − | − |
| 1-357 | − | − | * |
| 1-325 | − | − | * |
| 1-303 | − | − | * |
| 1-282 | − | − | * |
| 289-369 (most of ICD) | ++++ | +++ | − |
| 289-357 (12 aa deleted from the membrane distal domain) | ++ | * | * |
| 289-325 (44 aa deleted from the ICD) | ++ | * | * |

* Not tested

The results obtained with the different deletion mutants indicate that the membrane distal domain of cγc is involved in binding to NIK. Thus binding of a 41 amino acid polypeptide from the membrane distal domain of cγc, corresponding to residues 329-369 (dubbed 41 MDD) was analyzed.

TABLE E

| | Prey | | |
|---|---|---|---|
| Bait | cγc 329-369 (41 MDD polypeptide) | NIK624-947 (NIK C-terminus) | NIK |
| NIK624-947 (C-terminus) | +++ | * | * |
| NIK | + | * | * |
| cγc 329-369 (41 MDD polypeptide) | * | +/− | +/− |
| Lamin | − | − | − |

The binding of 41 MDD polypeptide to full length NIK or C-terminus NIK was tested in both orientations (i.e. 41 MDD as the pray and NIK as the bait and vice versa). The results obtained are shown in Table E. The interaction is relatively weak when NIK serves as the prey partner, but strong when NIK serves as the bait. The interaction of the 41 MDD is stronger with the C-terminus of NIK than with the full length NIK. These results confirmed that the 41 MDD polypeptide is involved in binding to NIK.

Similarly, two hybrid experiments were carried out with constructs comprising intracellular fragments located close to the membrane proximal domain (MPD) of cγc. The results suggested that a region of 44 amino acids, spanning amino acid residues 282-335 (44MPD) can also bind NIK.

Co-immunoprecipitation studies confirmed this results. The 44 MPD fused to GST and mycNIK were overexpressed in cells, the cells lysed and immunoprecipitated with anti GST (see Example 9). The immunoprecipitates were analyzed by western blots. The bound NIK was detected with antimyc antibodies. The results demonstrated that the 44 MPD fragment also binds NIK (not shown).

Mutagenesis studies were carried out in ICDcγc, in residues located at the 41 MDD, in order to define specific amino acids interacting with NIK. The interaction of proline rich motifs in signaling proteins with their cognate domains is well documented (Kay B K, Williamson M P, Sudol M. FASEB J 2000 Feb. 14 (2): 231-421). 20% of the amino acids in the 41 MDD amino acids are prolines. Therefore, two consecutive prolines were mutated to alanines at two different sites within the 41 MDD were mutated: 1—PP 336,337AA and 2—PP360, 361AA.

The mutation were carried out employing polymerase chain reaction (PCR) using the following primers:

For the generation of the PP336, 337AA mutants the following primers were used:

(SEQ ID NO: 7)
5' ctcgtcagtgagattgccgcaaaaggaggggcccttg (SEQ ID NO: 8)
5' caagggcccctccttttgcggcaatctcactgacgag For the generation of the PP360, 361AA mutants the following primers were used:

(SEQ ID NO: 9)
5' gcccctactgggccgccgcatgttacaccctaaag (SEQ ID NO: 10)
5' ctttagggtgtaacatgcggcggccagtaggggc In addition mutations were carried out in the 41 MDD in residues different from proline e.g. K338, E344 and W358.

For the generation of the K338A mutant the following primers were used:

(SEQ ID NO: 11)
5' gtcagtgagattcccccagcaggagggcccttggggag (SEQ ID NO: 12)
5' ctccccaagggcccctcctgctgggggaatctcactgac For the generation of the E344A mutant the following primers were used:

(SEQ ID NO: 13)
5' ggagggggcccttggggcggggcctggggcctcc (SEQ ID NO: 14)
5' ggaggccccaggcccgccccaagggcccctcc For the generation of the W358A mutant the following primers were used:

(SEQ ID NO: 15)
5' cagcatagcccctacgcggccccccccatgttac ((SEQ ID NO: 16)
5' gtaacatggggggccgcgtaggggctatgctg The mutated version of cγcICD were used as the bait and its interaction with NIK-C terminus was tested in the two hybrid system as described in Example 8.

TABLE F

| Bait | Prey-NIK624-947 (C-terminus) |
|---|---|
| cγc 289-369 (ICD) | ++++ |
| cγc289-369 (PP 336, 337AA) | +++ |
| cγc289-369 (PP 360, 361AA) | ++ |
| cγc289-369 K338A | +++ |
| cγc289-369 E344A | +++ |
| cγc289-369W358A | +++ |
| Lamin | − |
| TRAF2 | + |

The results are summarized in Table F. The replacement of prolines for alanine in residues 360 and 361 reduced the affinity to NIK by 50%, in contrast to other replacements, which failed to show substantial effect.

The results obtained of cyc mutagenesis demonstrate that the prolines at residues 360 and 361, which are located within the 41MDD region, are important for the binding to NIK.

Example 4

Effect of cyc and its Deletion Mutants on the NF-κB Induction Mediated by NIK Overexpression:

One experimental way to induce NF-κB activation in cells is by overexpressing NIK.

To check the effect of cyc on NF-κB activation mediated by NIK, cells were transiently transfected with the reporter plasmid encoding luciferase under the control of an NF-κB inducible promoter (pcDNA3 luciferase) and expression plasmids encoding NIK alone (pcS3MTNIK) or together with an expression plasmid encoding cyc (pcDNA3cyc). Activation of NF-κB was monitored by the luciferase reporter assay (for details see Example 10).

293-T cells were transfected with pcS3MTNIK and pcDNA3 luciferase. NF-κB activation was measured indirectly by measuring the luciferase activity present in the cells. To asses the effect of cyc on NIK mediated NF-κB activation pcDNA3cyc was co-transfected with pcS3MTNIK and pcDNA3 luciferase. Several cotransfections were carried out to test the effect of different concentrations of pcDNA3cyc with a constant concentration of pcS3MTNIK and pcDNA3 luciferase. 24 hours post transfection the cells were harvested, lysed and luciferase activity monitored.

The results of this experiment are summarized in FIG. 4. NIK overexpression alone induces expression of luciferase activity indicating that NF-κB is activated. This increase in luciferase activity was not observed in cells transfected with either the empty plasmid alone (pc) or the reporter gene and empty plasmid (pc+luc). The effect of cyc on NF-κB activation was found to depend on its concentration relative to NIK e.g. if cyc was expressed at lower concentrations than NIK, it potentiated NIK's effect (NIK 1 μg and cyc 0.1 μg plasmid DNA), while if present at equal or higher concentration, it inhibited NIK's effect (NIK 1 μg and cyc 1 μg plasmid DNA). Transfection of the cyc plasmid alone did not result in NF-κB activation (FIG. 5).

The C-terminus of NIK (residues 624-947) can be regarded as a dominant negative mutant (dnNIK) since it can bind to substrates and cyc (see Example 2), but is catalytically inactive. The effect of dnNIK overexpression on the enhancement in NF-κB activation observed in cell expressing low concentration of cyc and overexpressing NIK was monitored. The results are summarized in FIG. 5. As previously shown overexpression of NIK alone induced activation of NF-κB as evidenced by the increase in luciferase activity. Overexpression of dnNIK together with NIK inhibited this NF-κB activation. A further enhancement in NF-κB activation mediated by NIK was observed when cyc was expressed at low concentration. However, this enhancement of NF-κB activation was blocked by overexpression of dnNIK. This result confirms that the NF-κB inductive effect of cyc is exerted via NIK.

The human AlyNIK mutant (mutation in human is G860R corresponding to aly mutation in mouse G855R) was shown to bind cyc by the two-hybrid method (Example 2). Overexpression of this mutant alone induced NF-κB activation as efficient as the wild type NIK (FIG. 6). The effect of cyc on NF-κB activation mediated by aly NIK mutant was tested and is summarized in FIG. 6. Expression of cyc did not enhance NF-κB induction mediated by AlyNIK. Thus, despite that AlyNIK mutant is capable of binding cyc, its activity inducing NF-κB is not affected by cyc.

As shown above, the effect of full length cyc on NF-κB activation mediated by NIK overexpression is concentration dependent, e.g. to inhibit NIK mediated NF-κB activation a high or equal concentrations of cyc relative to NIK is required. In contrast, to enhance NIK mediated NF-κB activation, a low concentration of cyc relative to NIK is required.

The effect of overexpression of the 41 MDD (41 residues in the distal membrane domain of cyc, shown to bind NIK) on NIK induced and cyc enhanced NF-κB activation was tested.

Expression of intracellular cyc and fragments thereof in mammalian cells by transfection fails to give an appreciable amount of protein as evidenced by Western blot analysis (not shown). This may be due to the instability imposed by deletion of the transmembrane domain and extracellular domain. The intracellular domain contains a PEST domain, which might be exposed in the cycICD and fragments thereof and prone to proteases present in the cells. To solve this problem GST fusion of 41 MDD was generated to stabilize it and the effect of 41 MDD-GST fusion protein on NF-κB activation induced by NIK and cyc was tested.

150000 293-T cells were seeded per well in 6 well plates. 24 hours later the cells were transfected with a total DNA concentration at 3 μg/well (carrier DNA pcDNA). pcDNAcyc was used at a concentration of 50 ng/well to induce enhancement of NF-κB activity mediated by NIK. PcGST and a plasmid encoding the fusion protein GST-41MDD were used at high concentration 2 μg/well, pcS3MTNIK and pcDNA3luciferase at 0.5 μg/well. 24 hours post transfection, cells were harvested in 10011 extraction buffer and lysed by repeated freezing and thawing. Lysates were precleared by centrifugation (14000 rpm, microfuge 1 min.). Luciferase activity of 10 μl of the lysate was assayed in 360 μl of assay buffer. The results are summarized in FIG. 7. NF-κB induction is enhanced by overexpression of NIK and low expression of cyc. However, in a sample where the fusion protein GST-41 MDD is coexpressed with NIK and cyc, the activation levels of NF-κB are below the levels observed following overexpression of NIK alone. This result indicates that the 41 MDD, similar to the whole cyc, inhibits NIK dependent NF-κB activation when present at higher concentrations relative to NIK.

The effect of cyc and various mutants deleted at the C-terminal end of cyc (FIG. 1) on NF-κB activation induced by NIK was tested. The concentration of plasmid encoding the cyc and cyc mutants used was 0.5 μg/ml the same concentration as the plasmid encoding NIK. Under these conditions, the full-length cyc is expected to cause inhibition of NF-κB activation mediated by NIK.

150000 HeLa cells were seeded per well in 6 well plates. 24 hours later transfection was performed keeping the total DNA constant at 2 μg/well (pcDNA3 was used as carrier DNA). Plasmids encoding full-length cyc and all its deletion mutants were used at a concentration of 0.5 μg/well. NIK and luciferase encoding plasmids were also used at 0.5 μg/well. 24 hours post transfection, cells were harvested in 100 μl extraction buffer and lysed by repeated freezing and thawing. Lysates were precleared by centrifugation (14,000 rpm in a microfuge, 1 min.). Luciferase activities of the lysates were assayed in 360 μl of assay buffer.

The results are summarized in FIG. 8. Full-length cyc expressed at the same concentration as NIK inhibits NF-κB activity. Expressing cyc having progressive deletions in the membrane distal domain (FIG. 1), a domain that was shown to participate in binding to NIK, resulted in a concomitant decrease in inhibition of NF-κB activity. Deletion mutants with stop codons at residues 325 and 303 did not affect the activity of NIK.

These results confirm that the residues present in the membrane distal domain of cγc (from residues 325 to 369) participate in the binding of NIK and are important for modulating its activity.

Example 5

Effect cγc on the Kinase Activity of NIK:

In the previous examples it has been shown that cγc binds to NIK and modulates its activity. A possible mechanism underlying this regulation may be enhanced phosphorylation of NIK occurring upon cγc/NIK interaction.

To test the above hypothesis, NIK phosphorylation was assayed in-vitro in sample of cells overexpressing cγc alone (FIG. 9 lane 1), NIK alone (FIG. 9 lane 3 from the left), or NIK together with cγc (FIG. 9 lane 2 from the left), or NIK together with the kinase IKK (FIG. 9 lane 4 from the left) lysed and immunoprecipitated with anti NIK antibodies (For details see Example 11).

Kinase reaction was carried out with 5 μci γ $^{32}$P-ATP as previously described (Uhlik et al. 1998). The results in FIG. 9 show that cγc alone did not display any kinase activity (FIG. 9 lane 1 from the left). A three fold increase in phosphorylation of NIK self- and IKK1-phosphorylation was observed in the presence of cγc (compare lines 2 and 3). This result indicates that cγc may modulate the activity of NIK by inducing its phosphorylation.

Example 6

Effect of cγc in Modulating Signal Transduced Through the LTβ Receptor:

Induction of the LTβ receptor by its ligand, results in NF-κB activation. It is suggested in the literature that NIK participates in signaling through the LTβ receptor. Thus, the effect of overexpressing the whole cytoplasmic cγc polypeptide or the 41 distal domain (329-369) on NF-κB activation mediated by the LTβ receptor was tested. Activation of NF-κB was monitored by the luciferase reporter assay (for details see Example 10).

A cell line was prepared from mouse embryonic fibroblast cells, which are generally known to express the LTβ receptor. $10^5$ cells of the above line were seeded per well in 6 well plates. 24 hours later transfection was performed (with Gene porter transfection reagent, Gene therapy systems) with the plasmid pcGST ICDcγc expressing the intracellular domain of cγc (cγc ICD) fused to GST or with pcGST41MDD expressing the 41 distal domain of cγc fused to GST and the expression plasmid encoding luciferase reporter protein under the control of an NF-κB inducible promoter (pcDNA3 luciferase). NF-κB activation was measured indirectly by measuring the luciferase activity present in the cells.

Total DNA concentration was normalized to 2 μg/well with empty vector (pcDNA3). pcGST ICDcγc and pcGST41MDD were used at a concentration of about 1 μg/well. 24 hours after the transfection, cells were stimulated with 50 ng/ml recombinant LTβ (cat# L-5162, Sigma) for 1 hour.

The results are summarized in FIG. 10. Expression of the intracellular domain of cγc, enhanced the NF-κB activation by LTβ by 2.5 fold, while the expression of the membrane distal 41 amino acids inhibited by 50% NF-κB activation by LTβ.

The above results suggest that cγc may be involved in signaling through the LTβ receptor. The cγc 41 distal domain inhibits signaling through LTβ receptor, indicating that this polypeptide or fragments thereof may serve as candidates for peptide based drug designing. Such drugs may modulate NIK action and therefore are valuable in preventing or alleviating inflammatory responses or in modulatory immunoregulatory processes.

Example 7

Mapping the Region in NIK Involved in the Interaction with cγc:

The binding region in NIK was determined by testing the interaction of a series of NIK deletion mutants with cγc employing the yeast two-hybrid system. The truncated mutants of NIK were cloned into the pGBT9 two-hybrid bait vector and cγc was cloned into the pGADT7 prey vector. The binding was tested in the SFY526 heterologous yeast strain, by beta-gal assay. The results are summarized in Table G.

TABLE G

| Bait | Strength of interaction with Prey | | |
|---|---|---|---|
| | cγc | Traf2 | Lamin |
| NIK624-947 | ++++ | +++ | − |
| NIK | −/+ | + | − |
| NIK 1-367 | − | * | * |
| NIK 1-769 | − | * | * |
| NIK 1-820 | ++ | * | * |
| Lamin | − | − | * |

* Not tested

The results show that the cγc binding region in NIK resides in 196 amino acids at the C-terminus (residues 624-820).

To define more precisely the domain of NIK responsible for binding cγc, more deletion mutants of NIK were created and their binding to cγc was analysed by co-immunoprecipitation. 293T cells were transfected with vector encoding cγc and His tagged NIK deletion mutants and the binding of the different deletion mutants to cγc was tested by coimmunoprecipitation (see details in Example 9). Antibody against the cγc was used for immunoprecipitation and anti His antibodies were used to detect His-NIK deletion mutants of the immunoprecipitated material on Western blots. The results are summarized in Table H.

TABLE G

| Construct | Binding to cγc |
|---|---|
| NIK 1-947 (full length) | + |
| NIK 1-821 | + |
| NIK 1-771 | + |
| NIK 1-720 | + |
| NIK 1-640 | − |

The results indicate that a domain of NIK comprising 81 amino acid residues, located between amino acids 640 and 720 (SEQ ID NO: 18), is responsible for binding cγc.

Example 8

The Two Hybrid System Method:

The two-Hybrid system used for screening was the MATCHMAKER version III (Clontech). In this system the bait gene (NIK gene) is expressed as a fusion to the GAL4 DNA binding domain DNA-BD), while the prey genes or cDNA library is expressed as a fusion to the GAL4 activation domain (AD). When the DNA-BD and AD are brought into proximity, transcription of four reporter genes is activated (encoding HIS, ADE, lacZ and α-gal).

A human bone marrow library (Clontech cat# HY4053AH) has been selected as the prey, based on evidences indicating a pivotal role of NIK in the lymphoid system development and function.

Clones are grown on plates under high stringency conditions, i.e. in plates without LEU (selection marker for the bait encoding plasmid), TRP (selection marker for the prey encoding plasmid), HIS and ADE and impregnated with substrates for detection of α-gal expression. Plasmids were purified from positive clones by lysis of the yeast cells (with detergent and mechanical stress) followed by phenol extraction and ethanol precipitation of the DNA. cDNA inserts in the plasmids were amplified by PCR with flanking primers specific for the library vector pACT2. Individual amplified cDNAs were directly cloned into a mammalian expression vector for further biochemical analysis.

Example 9

Immunoprecipitation Method:

For transfection 1.5 million 293-T cells were seeded into 10 cm plates. 24 hours later, calcium phosphate assisted cotransfection (Molecular Cloning $2^{nd}$ edition 15.33) was carried out with myc tagged NIK and cγc expression plasmids, maintaining a total DNA concentration of 20 μg per plate. 30 hours later, cells were harvested and lysed in 1% NP-40 lysis buffer (0.5% NP-40, 10 mM Tris (PH 7.5), 150 nM NaCl, 1 mM EDTA). Immunoprecipitations were carried out by incubating 16 hours with the respective antibodies (rabbit polyclonal from Santa Cruz) directed either against the C-termini of cγc or directed against NIK which were pre-adsorbed to protein A sparse (rabbit polyclonal) or protein G sparse (mouse monoclonal). Immunoprecipitates were washed three times with lysis buffer and once with buffered saline. Beads were boiled in 40 μl of Laemmli sample buffer and 20 μl loaded in 10% SDS/PAGE. Proteins were blotted from the gel to a PVDF membrane and probed with anti cγc and anti NIK, followed by Goat anti rabbit antibody conjugated with horseradish peroxidase. Blots were developed by Enhanced Chemi Luminiscence (ECL) using Luminol (cat A8511, Sigma) as substrate.

Example 10

NIK Mediated NF-κB Activation Assay:

293-T cells ($1.5 \times 10^5$ per well in 6-well plate) were transfected with the total DNA amount of 3 μg per well. When needed the empty vector pCDNA was used as carrier DNA. Cotransfections were carried out as described in Example 9 with 1 μg of pcS3MTNIK and 0.5 μg of pcDNA3 vector expressing luciferase under the control of HIV-LTR (Human immunodeficiency virus long terminal repeats), a promoter upregulated by NF-κB. DNA encoding the cγc (pcDNA cγc) was introduced into pcDNA and used at 1/10, 1/2, and 1/1 ratio of the NIK expression vector concentration (the vectors have about the same molecular weight) 24 hours post transfection, cells were harvested in 100 μl extraction buffer (0.1 M potassium phosphate, pH 7.8, 1 mM DTT) and lysed by repeating freezing and thawing (Liquid nitrogen and 1 min. at 22° C.). Lysates were pre-cleared by centrifugation (14,000 rpm, microfuge, 1 min.). Luciferase activity of 5 μl lysate was assayed in 360 μl buffer (20 mM potassium phosphate, 20 mM Glycil-Glycine, 8.5 μM Magnesium sulphate, 2 mM EGTA, 1 mM DTT, 1 mM ATP and 5 μM D-luciferin (cat L-6882, Sigma).

Example 11

Kinase Assay:

293-T cells ($2 \times 10^6$ per 10 cm plate) were transfected by the calcium phosphate method with 10 μg of pcS3MTNIK and 10 μg of pcDNAcγc or histidine tagged IKK1 (pcHISIKK1) maintaining total DNA concentration of 20 μg per plate using empty pcDNA as the carrier DNA. 24 hours later, cells were harvested and lysed in 1% NP-40 lysis buffer and immunoprecipitation carried out for 8 hours with rabbit anti NIK antibody pre-adsorbed to protein A sepharose beads. Kinase reaction was carried out with 5 μci γ $^{32}$P-ATP as previously described (Uhlik et al. 1998).

Example 12

Preparation and Screen of Non Peptide Small Molecules Inhibiting NIK-cγc Interaction:

A library of small non peptide molecules are prepared by combinatorial chemistry. The design of combinatorial chemistry technology is well known in the art and is described e.g. by Hermkens et al. (1996). Cells expressing NIK, cγc and the reporter plasmid encoding luciferase under the control of an NF-κB inducible promoter (pcDNA3 luciferase) are exposed to individual synthetic organic compounds and NF-kb activation is tested as described in example 4.

Compounds able to inhibit NF-kb activation are selected for future testing.

Alternatively, cells are transiently transfected with cγc and the reporter plasmid encoding luciferase under the control of an NF-κB inducible promoter (pcDNA3 luciferase) and exposed to individual synthetic organic compounds. Following exposure to synthetic compounds, NF-κB activation is tested as described in example 6 when endogenous NIK is activated by ligand binding to the corresponding receptor.

Compounds able to inhibit NF-κB activation are selected for future testing.

Example 13

Interaction of Endogenous NIK and cγc.

NIK and cγc interaction was demonstrated in a mammalian cell environment, in lysates of 293-T cells overexpressing these proteins (see Example 4). The following experiment was carried with endogenous proteins, in cells naturally expressing these proteins. Thus, peripheral blood mononuclear cells (PMBC) ($500 \times 10^6$ cells) were incubated with IL-2, lysed and immunoprecipitated with anti cγc antibodies (for immunoprecipitation see Example 9). Co-immunoprecipitated proteins bound to cγc were detected in Western blots using relevant antibodies. The candidate proteins tested for co-immunoprecipitation with cγc were those proteins normally present in the signalosome, such as NIK, IKKα (IKK-1), IKKβ (IKK2), IKKγ (NEMO). The co-immunoprecipitated proteins were tested in lysates of cells tested at time-0 and after four-hour incubation with IL-2. The results summarized in FIG. 16A show that NIK is coprecipitated with cγc before and after stimulation with IL-2. Therefore NIK was found constitutively associated with cγc. Traces of IKK-1 was found in the basal level and upon 4 hours incubation with IL-2, other signalosome components, i.e. IKK-2 and NEMO, were recruited to the IL-2 receptor through the cγc. The results indicate that the IL-2 receptor gamma chain is bound to NIK at a different location than the IKK-1 binding region. Similar results were obtained upon stimulation of the cells with IL-15 (FIG. 16A right panel).

To check whether the signalosome co-immunoprecipitated with cγc are active, the above immunoprecipitates were tested in a kinase assay (see details in Example 11) which monitors phosphorylation of GST-IκBα1-54. The results summarized in FIG. 16 B indicated that only immunoprecipitates from cells stimulated with IL-2 are capable of phosphorylating GS-IK Bα1-54.

Thus these results demonstrate that under physiological conditions, NIK is constitutively associated to cγc, and that this interaction is involved in IL-2 signalling and NIK dependent NF-κB activation. Therefore inhibiting of cγc and NIK interaction will result in the inhibition of IL-2 signaling activities and inhibition of NIK induced NF-κB activation.

References

Akiba, H., Nakano, H., Nishinaka, S., Shindo, M., Kobata, T., Atsuta, M., Morimoto, C., Ware, C. F., Malinin, N. L., Wallach, D., Yagita, H., and Okumura, K. (1998). CD27, a member of the tumor necrosis factor receptor superfamily, activates NF-kappaB and stress-activated protein kinase/c-Jun N-terminal kinase via TRAF2, TRAF5, and NF-kappaB-inducing kinase. *J Biol Chem* 273, 13353-8.

Baldwin, A. S., Jr. (1996). The NF-kappa B and I kappa B proteins: new discoveries and insights. *Annu Rev Immunol* 14, 649-83.

Canicio, J., Ruiz-Lozano, P., Carrasco, M., Palacin, M., Chien, K., Zorzano, A., and Kaliman, P. (2001). Nuclear factor kappa B-inducing kinase and Ikappa B kinase-alpha signal skeletal muscle cell differentiation. *J Biol Chem* 276, 20228-33.

Darnay, B. G., Ni, J., Moore, P. A., and Aggarwal, B. B. (1999). Activation of NF-kappaB by RANK requires tumor necrosis factor receptor-associated factor (TRAF) 6 and NF-kappaB-inducing kinase. Identification of a novel TRAF6 interaction motif. *J Biol Chem* 274, 7724-31.

DiSanto, J. P., Muller, W., Guy-Grand, D., Fischer, A., and Rajewsky, K. (1995). Lymphoid development in mice with a targeted deletion of the interleukin 2 receptor gamma chain. *Proc Natl Acad Sci USA* 92, 377-81.

Fagarasan, S., Shinkura, R., Kamata, T., Nogaki, F., Ikuta, K., Tashiro, K., and Honjo, T. (2000). Alymphoplasia (aly)-type nuclear factor kappaB-inducing kinase (NIK) causes defects in secondary lymphoid tissue chemokine receptor signaling and homing of peritoneal cells to the gut-associated lymphatic tissue system. *J Exp Med* 191, 1477-86.

Fields, S. and Song, O. (1989). A novel genetic system to detect protein-protein interactions. *Nature* 340, 245-6.

Foehr, E. D., Bohuslav, J., Chen, L. F., DeNoronha, C., Geleziunas, R., Lin, X., O'Mahony, A., and Greene, W. C. (2000). The NF-kappa B-inducing kinase induces PC12 cell differentiation and prevents apoptosis. *J Biol Chem* 275, 34021-4.

Garceau, N., Kosaka, Y., Masters, S., Hambor, J., Shinkura, R., Honjo, T., and Noelle, R. J. (2000). Lineage-restricted function of nuclear factor kappaB-inducing kinase (NIK) in transducing signals via CD40. *J Exp Med* 191, 381-6.

Geleziunas, R., Ferrell, S., Lin, X., Mu, Y., Cunningham, E. T., Jr., Grant, M., Connelly, M. A., Hambor, J. E., Marcu, K. B., and Greene, W. C. (1998). Human T-cell leukemia virus type 1 Tax induction of NF-kappaB involves activation of the IkappaB kinase alpha (IKKalpha) and IKKbeta cellular kinases. *Mol Cell Biol* 18, 5157-65.

Ghosh, S., May, M. J., and Kopp, E. B. (1998). NF-kappa B and Rel proteins: evolutionarily conserved mediators of immune responses. *Annu Rev Immunol* 16, 225-60.

Hermkens P H and Adang A E, (1996). The contribution of combinatorial chemistry to lead generation: an interim analysis. Curr Med Chem 2001 July; 8(9):985-98

Karin, M. and Ben-Neriah, Y. (2000). Phosphorylation meets ubiquitination: the control of NF-[kappa]B activity. *Annu Rev Immunol* 18, 621-63.

Leonard, W. J., Shores, E. W., and Love, P. E. (1995). Role of the common cytokine receptor gamma chain in cytokine signaling and lymphoid development. *Immunol Rev* 148, 97-114.

Lin, X., Cunningham, E. T., Jr., Mu, Y., Geleziunas, R., and Greene, W. C. (1999). The proto-oncogene Cot kinase participates in CD3/CD28 induction of NF-kappaB acting through the NE-kappaB-inducing kinase and IkappaB kinases. *Immunity* 10, 271-80.

Ling, L., Cao, Z., and Goeddel, D. V. (1998). NF-kappaB-inducing kinase activates IKK-alpha by phosphorylation of Ser-176. *Proc Natl Acad Sci USA* 95, 3792-7.

Malinin, N. L., Boldin, M. P., Kovalenko, A. V., and Wallach, D. (1997). MAP3K-related kinase involved in NF-kappaB induction by TNF, CD95 and IL-1. *Nature* 385, 540-4.

Matsumoto, M., Iwamasa, K., Rennert, P. D., Yamada, T., Suzuki, R., Matsushima, A., Okabe, M., Fujita, S., and Yokoyama, M. (1999). Involvement of distinct cellular compartments in the abnormal lymphoid organogenesis in lymphotoxin-alpha-deficient mice and alymphoplasia (aly) mice defined by the chimeric analysis. *J Immunol* 163, 1584-91.

Matsushima, A., Kaisho, T., Rennert, P. D., Nakano, H., Kurosawa, K., Uchida, D., Takeda, K., Akira, S., and Matsumoto, M. (2001). Essential role of nuclear factor (NF)-kappaB-inducing kinase and inhibitor of kappaB (IkappaB) kinase alpha in NF-kappaB activation through lymphotoxin beta receptor, but not through tumor necrosis factor receptor I. *J Exp Med* 193, 631-6.

Mercurio, F. and Manning, A. M. (1999). Multiple signals converging on NF-kappaB. *Curr Opin Cell Biol* 11, 226-32.

Miyawaki, S., Nakamura, Y., Suzuka, H., Koba, M., Yasumizu, R., Ikehara, S., and Shibata, Y. (1994). A new mutation, aly, that induces a generalized lack of lymph nodes accompanied by immunodeficiency in mice. *Eur J Immunol* 24, 429-34.

Natoli, G., Costanzo, A., Moretti, F., Fulco, M., Balsano, C., and Levrero, M. (1997). Tumor necrosis factor (TNF) receptor 1 signaling downstream of TNF receptor-associated factor 2. Nuclear factor kappaB (NFkappaB)-inducing kinase requirement for activation of activating protein 1 and NFkappaB but not of c-Jun N-terminal kinase/stress-activated protein kinase. *J Biol Chem* 272, 26079-82.

Noguchi, M., Yi, H., Rosenblatt, H. M., Filipovich, A. H., Adelstein, S., Modi, W. S., McBride, O. W., and Leonard, W. J. (1993). Interleukin-2 receptor gamma chain mutation results in X-linked severe combined immunodeficiency in humans. *Cell* 73, 147-57.

Pahl, H. L. (1999). Activators and target genes of Rel/NF-kappaB transcription factors. *Oncogene* 18, 6853-66.

Regnier, C. H., Song, H. Y., Gao, X., Goeddel, D. V., Cao, Z., and Rothe, M. (1997). Identification and characterization of an IkappaB kinase. *Cell* 90, 373-83.

Rothe, M., Wong, S. C., Henzel, W. J., and Goeddel, D. V. (1994). A novel family of putative signal transducers associated with the cytoplasmic domain of the 75 kDa tumor necrosis factor receptor. *Cell* 78, 681-92.

Senftleben, U., Cao, Y., Xiao, G., Greten, F. R., Krahn, G., Bonizzi, G., Chen, Y., Hu, Y., Fong, A., Sun, S. C., and Karin, M. (2001). Activation by IKKalpha of a second, evolutionary conserved, NF-kappa B signaling pathway. *Science* 293, 1495-9.

Shinkura, R., Kitada, K., Matsuda, F., Tashiro, K., Ikuta, K., Suzuki, M., Kogishi, K., Serikawa, T., and Honjo, T. (1999). Alymphoplasia is caused by a point mutation in the mouse gene encoding Nf-kappa b-inducing kinase. *Nat Genet* 22, 74-7.

Smith, G. P. (1985). Filamentous fusion phage: novel expression vectors that display cloned antigens on the virion surface. *Science* 228, 1315-7.

Sylla, B. S., Hung, S. C., Davidson, D. M., Hatzivassiliou, E., Malinin, N. L., Wallach, D., Gilmore, T. D., Kieff, E., and Mosialos, G. (1998). Epstein-Barr virus-transforming protein latent infection membrane protein 1 activates transcription factor NF-kappaB through a pathway that includes the NF-kappaB-inducing kinase and the IkappaB kinases IKKalpha and IKKbeta *Proc Natl Acad Sci USA* 95, 10106-11.

Takeuchi, M., Rothe, M., and Goeddel, D. V. (1996). Anatomy of TRAF2. Distinct domains for nuclear factor-kappaB activation and association with tumor necrosis factor signaling proteins. *J Biol Chem* 271, 19935-42.

Uhlik, M., Good, L., Xiao, G., Harhaj, E. W., Zandi, E., Karin, M., and Sun, S. C. (1998). NF-kappaB-inducing kinase and IkappaB kinase participate in human T-cell leukemia virus I Tax-mediated NF-kappaB activation. *J Biol Chem* 273, 21132-6.

Xiao, G., Harhaj, E. W., and Sun, S. C. (2001). NF-kappaB-inducing kinase regulates the processing of NF-kappaB2 p100. *Mol Cell* 7, 401-9.

Xiao, G. and Sun, S. C. (2000). Negative regulation of the nuclear factor kappa B-inducing kinase by a cis-acting domain. *J Biol Chem* 275, 21081-5.

Yamada, T., Mitani, T., Yorita, K., Uchida, D., Matsushima, A., Iwamasa, K., Fujita, S., and Matsumoto, M. (2000). Abnormal immune function of hemopoietic cells from alymphoplasia (aly) mice, a natural strain with mutant NF-kappa B-inducing kinase. *J Immunol* 165, 804-12.

Yamamoto and Gaynor. The Journal of Clinical Investigation (2001) 107:135-142.

Yin, L., Wu, L., Wesche, H., Arthur, C. D., White, J. M., Goeddel, D. V., and Schreiber, R. D. (2001). Defective lymphotoxin-beta receptor-induced NF-kappaB transcriptional activity in NIK-deficient mice. *Science* 291, 2162-5.

---

We claim:

1. An isolated NF-KB inducing kinase (NIK) polypeptide fragment that binds to 41 MDD (SEQ ID NO:2) or 44 MPD (SEQ ID NO:17), said fragment selected from the group consisting of:
   (a) a polypeptide consisting essentially of an amino acid sequence that is at least 75% identical to SEQ ID NO:18, and which binds to 41 MDD or 41 MPD; and
   (b) a salt or functional derivative of (a) that binds to 41MDD or 44 MPD, said functional derivative being an ester or aliphatic amide of a carboxyl group of the polypeptide or an N-acyl derivative of a free amino group of the polypeptide, or an O-acyl derivative of a free hydroxyl group of the polypeptide, or a derivative obtained by linking the polypeptide to polyethylene glycol, or a combination thereof.

2. The isolated NF-KB inducing kinase (NIK) polypeptide fragment of claim 1, said fragment selected from the group consisting of:
   (a) the polypeptide consisting of SEQ ID NO:18; and
   (b) a salt or functional derivative of (a) that binds to 41 MDD or 44 MPD, said functional derivative being an ester or aliphatic amide of a carboxyl group of the polypeptide or an N-acyl derivative of a free amino group of the polypeptide, or an O-acyl derivative of a free hydroxyl group of the polypeptide, or a derivative obtained by linking the polypeptide to polyethylene glycol, or a combination thereof.

3. The polypeptide of claim 1, consisting of the polypeptide of SEQ ID NO: 18.

4. The polypeptide of claim 1, wherein said polypeptide of (a) is SEQ ID NO:18 or a polypeptide that differs from SEQ ID NO:18 solely by one or more amino acid substitutions.

5. The polypeptide of claim 4 wherein said substitutions are conservative substitutions in which one or more amino acids are replaced by different synonymous amino acids as set forth in the table A below:

| Amino Acid | Different Synonymous Amino Acid |
| --- | --- |
| Ser | Thr, Gly, Asn |
| Arg | Gln, Lys, Glu, His |
| Leu | Ile, Phe, Tyr, Met, Val |
| Pro | Gly, Ala, Thr |
| Thr | Pro, Ser, Ala, Gly, His, Gln |
| Ala | Gly, Thr, Pro |
| Val | Met, Tyr, Phe, Ile, Leu |
| Gly | Ala, Thr, Pro, Ser |
| Ile | Met, Tyr, Phe, Val, Leu |
| Phe | Trp, Met, Tyr, Ile, Val, Leu |
| Tyr | Trp, Met, Phe, Ile, Val, Leu |
| Cys | Ser, Thr |
| His | Glu, Lys, Gln, Thr, Arg |
| Gln | Glu, Lys, Asn, His, Thr, Arg |
| Asn | Gln, Asp, Ser |
| Lys | Glu, Gln, His, Arg |
| Asp | Glu, Asn |
| Glu | Asp, Lys, Asn, Gln, His, Arg |
| Met | Phe, Ile, Val, Leu |

6. The polypeptide of claim 4 wherein said substitutions are conservative substitutions in which one or more amino acids are replaced by different synonymous amino acids as set forth in the table B below:

| AminoAcid | Different Synonymous Amino Acid |
| --- | --- |
| Arg | His, Lys |
| Leu | Ile, Phe, Met |
| Pro | Ala |
| Ala | Pro |
| Val | Met, Ile |
| Ile | Met, Phe, Val, Leu |
| Phe | Met, Tyr, Ile, Leu |
| Tyr | Phe |
| Cys | Ser |
| His | Arg, Gln |
| Gln | Glu, His |
| Asn | Asp |
| Lys | Arg |
| Asp | Asn |
| Glu | Gln |
| Met | Phe, Ile, Val, Leu |

7. The polypeptide of claim 4 wherein said substitutions are conservative substitutions in which one or more amino acids are replaced by different synonymous amino acids as set forth in the table C below:

| Amino Acid | Different Synonymous Amino Acid |
| --- | --- |
| Leu | Ile, Met |
| Ile | Met, Leu |
| Cys | Ser |
| Met | Ile, Leu. |

8. The polypeptide of claim 1, wherein the polypeptide of (b) is identical to SEQ ID NO:18, or differs from SEQ ID NO:18 by deleting, adding or replacing with a different amino acid a total of up to 12% of the amino acid residues of SEQ ID NO:18.

* * * * *